US010434166B2

(12) United States Patent
Perez et al.

(10) Patent No.: US 10,434,166 B2
(45) Date of Patent: *Oct. 8, 2019

(54) METHODS AND COMPOSITIONS FOR IN VIVO IMMUNE STIMULATION AND ANTIGEN PRODUCTION

(71) Applicant: University of Maryland, College Park, MD (US)

(72) Inventors: Daniel R. Perez, Olney, MD (US); Hongjun Chen, Hayttsville, MD (US)

(73) Assignee: UNIVERSITY OF MARYLAND, COLLEGE PARK, College Park, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/777,442

(22) PCT Filed: Mar. 15, 2014

(86) PCT No.: PCT/US2014/029994
§ 371 (c)(1),
(2) Date: Sep. 15, 2015

(87) PCT Pub. No.: WO2014/145261
PCT Pub. Date: Sep. 18, 2014

(65) Prior Publication Data
US 2016/0022807 A1 Jan. 28, 2016

Related U.S. Application Data

(60) Provisional application No. 61/787,171, filed on Mar. 15, 2013.

(51) Int. Cl.
*A61K 39/145* (2006.01)
*C12N 7/00* (2006.01)
*A61K 39/12* (2006.01)

(52) U.S. Cl.
CPC ............ *A61K 39/145* (2013.01); *A61K 39/12* (2013.01); *C12N 7/00* (2013.01); *C12N 2710/14041* (2013.01); *C12N 2760/16034* (2013.01); *C12N 2760/16134* (2013.01)

(58) Field of Classification Search
CPC ........ A61K 39/145; A61K 2039/55555; A61K 39/155; A61K 2039/53; C12N 2760/16011; C12N 9/1247; C12N 15/86; C12N 2760/16143; C12N 2760/16162; C12N 2760/16243; C12N 2760/16262; C12N 2760/18122; C12N 2760/18151; C12N 2799/021; C12N 2760/16151; C12N 2760/16152; C12N 2760/16034; C12N 9/01; G01N 2333/11; G01N 33/56983

See application file for complete search history.

(56) References Cited

U.S. PATENT DOCUMENTS

| 7,045,136 B1 * | 5/2006 | Moss ................... A61K 39/285 424/199.1 |
| 7,951,383 B2 * | 5/2011 | Murphy ............... A61K 39/155 424/211.1 |
| 9,463,237 B2 * | 10/2016 | Falkner ................ A61K 39/145 |
| 2012/0107911 A1 * | 5/2012 | Liu ...................... A61K 39/145 435/235.1 |
| 2012/0270321 A1 | 10/2012 | Dormitzer et al. |

FOREIGN PATENT DOCUMENTS

| WO | WO2012106231 | * | 8/2012 |
| WO | WO-2014/145261 A2 | | 9/2014 |

OTHER PUBLICATIONS

Song et al. Journal of Virol. 2007, 81(17): 9238-9248.*
Prabakaran (A) Antiviral Research 2010, 86(2), 180-187.*
Prabakaran (B) Virology, 2008, vol. 380, Issue 2, pp. 412-420.*
Schickli et al. Phil. Trans. R. Soc. Lond. B. 2001, vol. 356, pp. 1965-1973.*
Cheng, G. et al., An In Vivo Transfection Approach Elucidates a Role for *Aedes aegypti* Thioester-Containing Proteins in Flaviviral Infection. PLoS One. 2011; 6(7):e22786 (7 pages).
Pinel, K. et al., Long-term in vivo Imaging of Translated RNAs for Gene Therapy. Gene Therapy. 2014; 21(4):434-9.
Tretyakova, I. et al., Plasmid DNA Initiates Replication of Yellow Fever Vaccine in V

(56) References Cited

OTHER PUBLICATIONS

PCT, PCT/US2014/029994 (WO 2014/145261), Mar. 15, 2014 (Sep. 18, 2014), Perez et al. (University of Maryland).
Yamamoto, M. et al., In Vivo Transfection of Hepatitis C Virus Complementary DNA into Rodent Liver by Asialoglycoprotein Receptor Mediated Gene Delivery. Hepatology. 1995; 22(3):847-55.

* cited by examiner

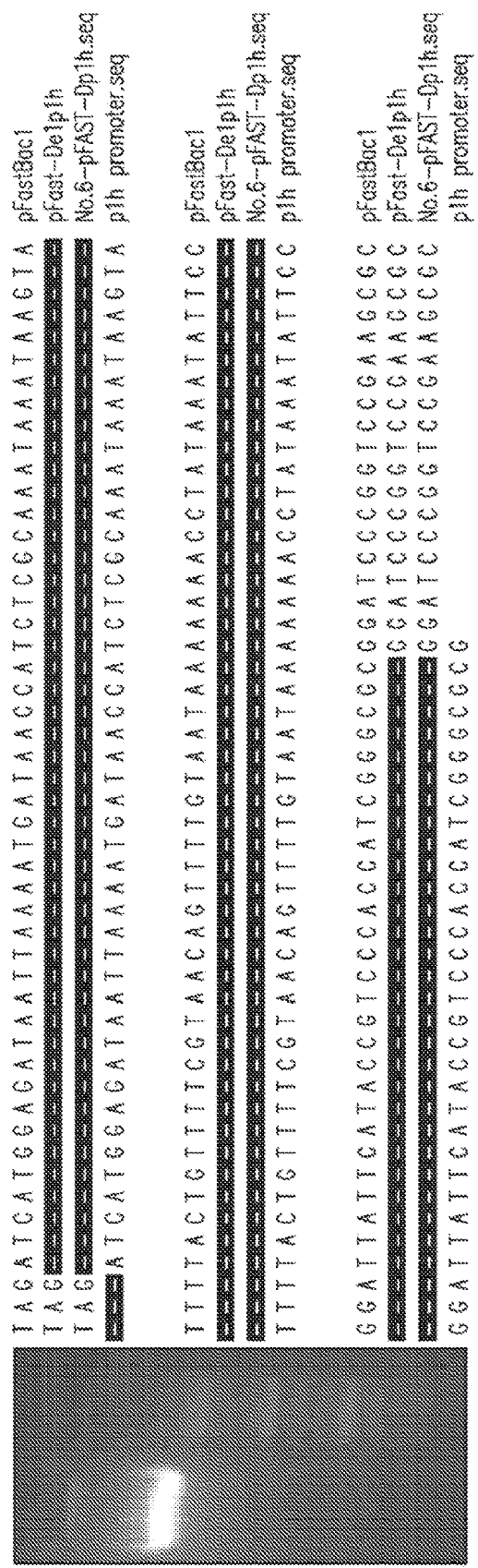
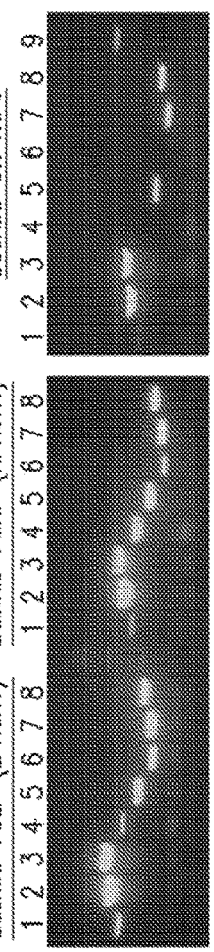
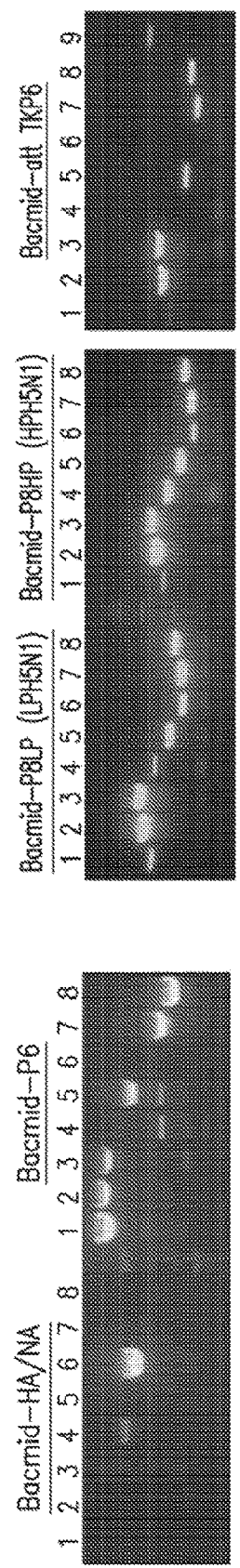
FIG. 5A
FIG. 5B
FIG. 5C

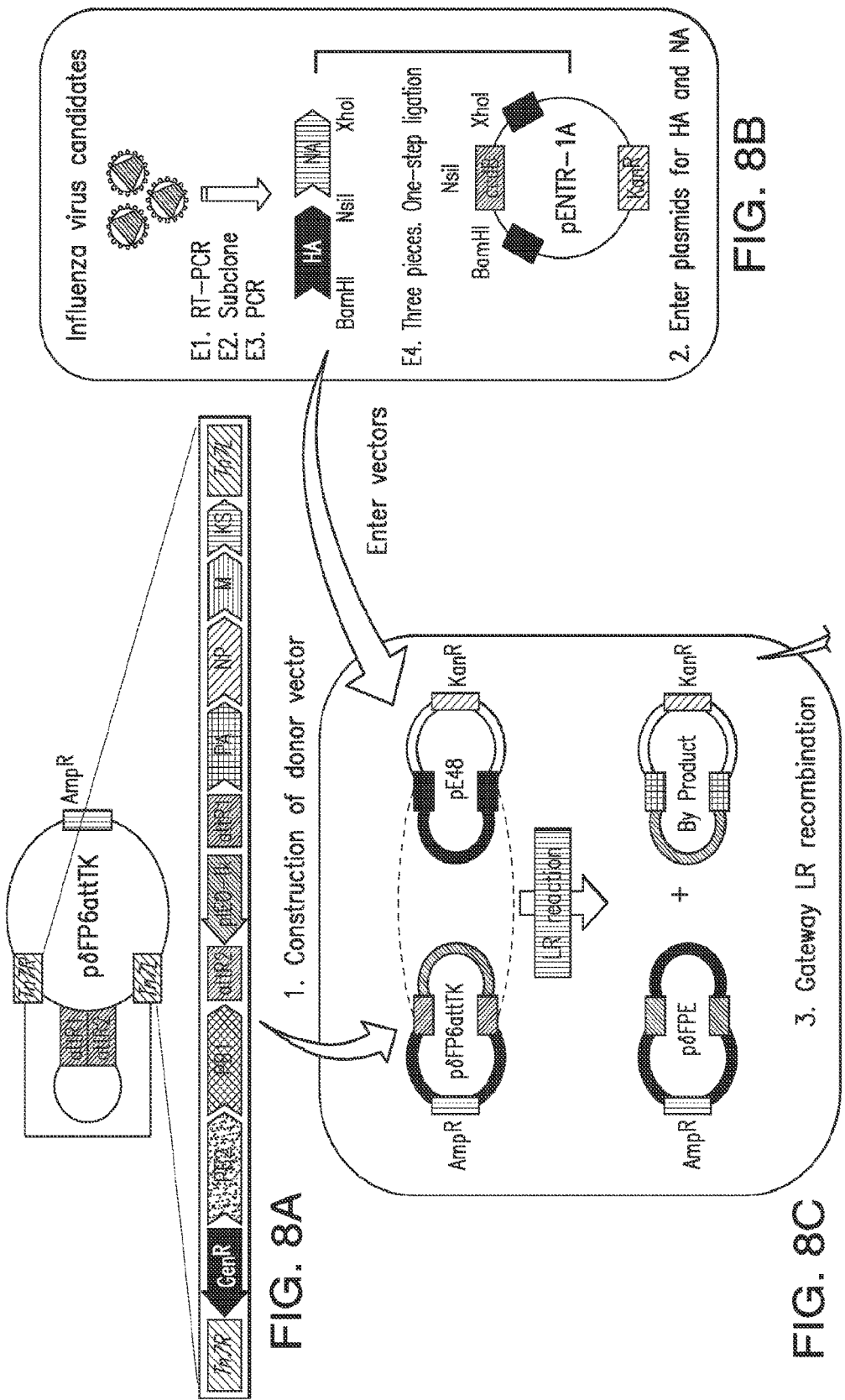

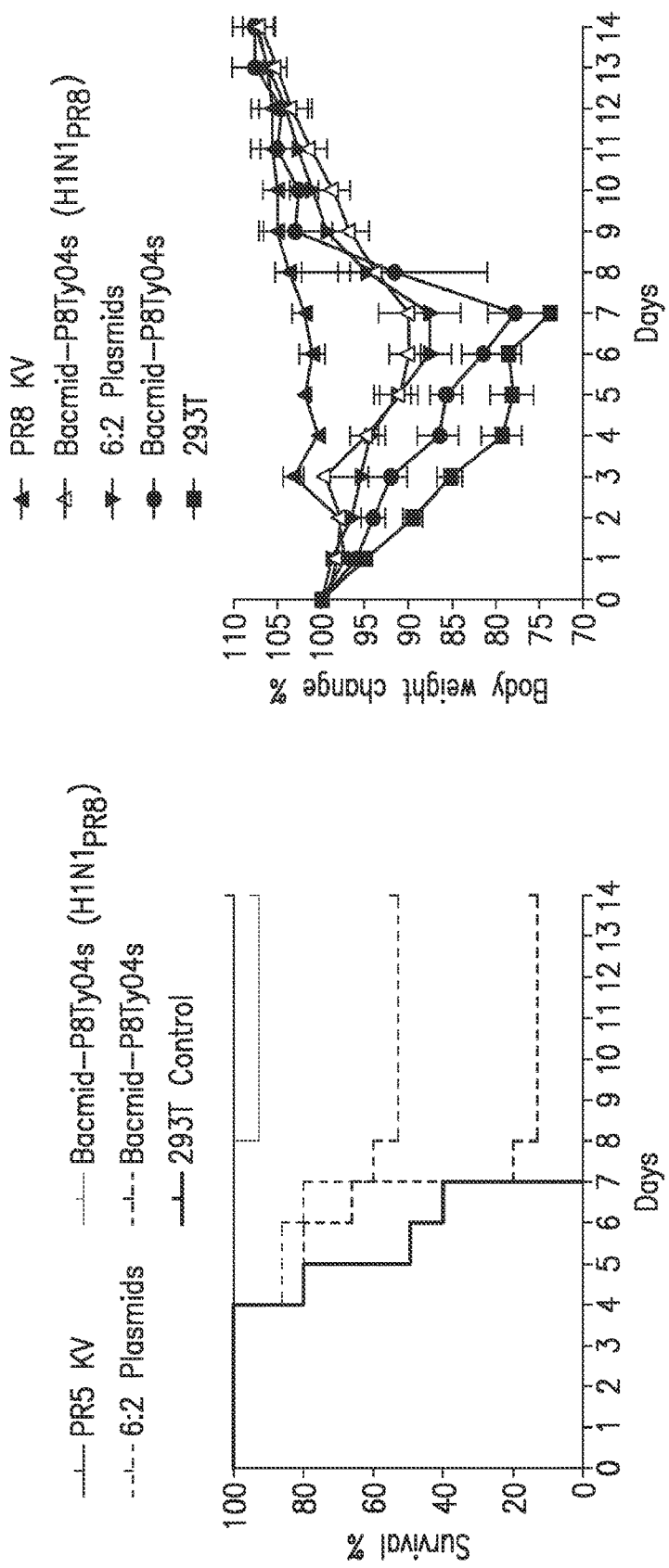

METHODS AND COMPOSITIONS FOR IN VIVO IMMUNE STIMULATION AND ANTIGEN PRODUCTION

CROSS-REFERENCE TO RELATED APPLICATIONS

This application is a National Phase Under 35 U.S.C. § 371 of PCT/US2014/029994 filed in the Patent Cooperation Treaty U.S. Receiving Office on Mar. 15, 2014, which claims the benefit of U.S. Provisional Application No. 61/787,171, filed Mar. 15, 2013, the entire contents of which are herein incorporated by reference.

REFERENCE TO SEQUENCE LISTING

The Sequence Listing submitted Dec. 4, 2017 as a text file named "36429_0006U1_Updated_Sequence_Listing.txt," created on Dec. 4, 2017, and having a size of 13,308 bytes is hereby incorporated by reference pursuant to 37 C.F.R. § 1.52(e)(5).

FIELD OF THE INVENTION

The disclosed invention is generally in the field of molecular biology and specifically in the area of virology.

BACKGROUND

Prevention of disease in humans and animals is often aided by immunizing a population of such subjects to enable the subjects' immune system to respond to the antigenic components of the pathogenic system. Though such immune stimulation or vaccination therapies have been in use for hundreds of years, pathogenic agents continue cause worldwide economic losses and much loss of life for humans and animals. For example, influenza epidemics continue to be a major disease burden in both animals and humans, with approximately 5-15% of the human population infected on an annual basis. Severe influenza disease is estimated to affect 3-5 million people worldwide, and is associated with 250,000 500,000 deaths annually. Despite efforts to curtail the emergence of novel pandemic influenza strains, an influenza virus of swine origin was responsible for a pandemic of influenza in 2009. Vaccination provides an effective means for control of influenza and it is considered the first line of defense against it. Human influenza vaccines are produced as either split virion inactivated (killed vaccines, KV) or live attenuated vaccines (LAIV). These vaccines are reformulated every year due to the virus' ability to undergo antigenic drift and escape the immunological pressure developed against previous strains.

Manufacture of vaccines or immune therapeutics is often limited by the need to grow pathogenic agents in in vitro cultures that are not ideal for the reproduction of the pathogenic agent. For example, a major drawback in the preparation of LAIV and KV influenza vaccines is that production relies on a time-consuming process of growing the viruses in eggs or tissue culture cells. Additionally, since most human influenza strains grow poorly in these systems, vaccine strains are produced from reassortants that generally carry the surface gene segments from the candidate virus and other segments from a high growth donor virus. Reverse genetics (RG) has improved the ability to generate such high growth reassortants (Neuman et al. Virology 287:243-250 (2001), Maassab et al. Rev Med Virol 9:237-244 (1999); however, growing influenza viruses in eggs or tissue culture may result in adaptive changes on the viral surface proteins resulting in antigenic mismatch. LAIV vaccines have an advantage over KV vaccines since they produce broader responses by stimulating both the humoral and the T-cell arms of the immune system (Ambrose et al. Inf Other Resp Viruses 2:193-202 (2008), Wareing et al. Vaccine 19:3320-3330 (2001)).

The 2009 pandemic H1N1 virus (pH1N1) highlighted the fact that these traditional vaccine production systems are too slow to significantly ameliorate or alter the impact of a pandemic given that the initial pH1N1 vaccine candidates were not well suited for growth in eggs (Chen et al. Journ of Infec Dis 203:930-936 (2011)). Furthermore, LAIV vaccines are not as effective in children under 2 or the elderly, which represent the groups at high risk of influenza infections. People with egg allergies cannot use egg-grown virus vaccines. Alternatively, egg-free influenza vaccine strategies have been investigated including recombinant viral proteins, recombinant viruses, and virus-like particles (VLPs) (Sedova et al. Recom Influenza Vaccines Acta Naturae 4:17-27 (2012)). FLUBLOK™, a baculovirus-based recombinant hemagglutinin influenza vaccine, is the only influenza vaccine approved for human use that does not rely on traditional production systems, but it must also undergo reformulation as a result of antigenic drift.

What is needed are methods and compositions for stimulating the immune system of a subject, such as by vaccine methods, wherein the antigenic composition or vaccine, does not need to be manufactured in tissue culture conditions, but instead, the vaccine composition is produced in the subject's body directly. What is needed are compositions and methods of treatment for reduction of infection by vaccination comprising vectors comprising polynucleotides that express pathogenic or oncogenic antigens that stimulate the immune system of a subject to whom the vector is provided.

BRIEF SUMMARY

The present invention comprises methods and compositions for stimulation of the immune system of a subject. The present invention comprises methods and compositions for producing pathogenic or oncogenic antigens. An aspect of the present invention comprises vaccination against pathogenic infections or oncogenic growth comprising in vivo reverse genetics. Similar to the concept of the "Trojan horse", aspects of the invention comprise providing a vector, such as a baculovirus vector or bacmid, that carries the necessary components for the synthesis of at least a portion of a pathogenic agent or oncogenic antigen in a subject. For example, a vector may comprise nucleic acid sequences that encode and express a live attenuated virus, such as a live attenuated influenza virus (LAIV), in vivo in one or more cells of a subject.

Vectors of the present invention may be delivered by administration methods known to those skilled in the art, including, but not limited to intramuscularly, intranasally, or orally, and may be provided in delivery vehicles including but not limited to, liposomes or cells. For example, provision to a subject of a vector comprising at least a portion of the genome of an influenza virus, results in the generation of live influenza virus in the host along with the stimulation of immune responses against influenza. Methods described herein enable attenuated components of a pathogen to be delivered directly to a host, along with the necessary components for the assembly of those components into a vaccine. Methods disclosed herein bypass the manufacturing step of having to generate a vaccine for a pathogenic organism or oncogenic antigen in an intermediary vehicle such as in vitro culture methods, for example, eggs.

Disclosed are methods and compositions for in vivo delivery of at least a portion of a genome and/or antigenic peptides of a pathogen comprising a vector and a reverse genetics competent unit of the pathogen. Disclosed are methods and compositions for in vivo delivery of at least a portion of one or more antigenic peptides or nucleic acids related to an oncogenic condition, for example, antigenic proteins associated with cancer, comprising a vector and a DNA construct expressing the antigenic proteins.

Disclosed are methods and compositions for in vivo delivery of at least a portion of a pathogen comprising a vector and a reverse genetics competent unit of a pathogen, wherein the vector comprises a bacmid, a baculovirus expression system, a synthetic vector, or a vector known to those skilled in the art. Disclosed are methods and compositions for in vivo delivery of a oncogenic antigen comprising a vector and a DNA construct expressing at least a portion of the oncogenic antigen, wherein the vector comprises a bacmid, a baculovirus expression system, a synthetic vector, or a vector known to those skilled in the art.

Disclosed are methods and compositions for in vivo delivery of at least a portion of a pathogen comprising a vector and a reverse genetics competent unit of the pathogen, wherein the pathogen comprises viral agents, bacterial agents and parasites. Disclosed are methods and compositions for in vivo delivery of at least a portion of an oncogenic antigen comprising a vector and a DNA construct that expresses an oncogenic antigen, wherein the oncogenic antigen comprises antigens associated with cancerous or oncogenic cells, for example tumor antigens or oncogenic proteins or oncoproteins. A tumor antigen is an antigenic substance produced in tumor cells, i.e., it triggers an immune response in the host. Tumor antigens are useful tumor markers in identifying tumor cells with diagnostic tests and are candidates for use in cancer therapy. Immune responses to oncogenic proteins are known. Immunity to nonmutated overexpressed oncoproteins as well as to mutated or unique cancer-specific oncoproteins has been identified. Immune system based treatments targeting oncogenic proteins have shown therapeutic efficacy in animals models and are undergoing human trials. As used herein, oncogenic proteins or oncoproteins includes, but is not limited to, nonmutated overexpressed proteins, mutated proteins, or cancer-specific proteins.

Disclosed are methods and compositions for in vivo delivery of an immunogenic composition that stimulates an immune response to at least a portion of influenza comprising a vector wherein the vector comprises a recombinant baculovirus vector and a reverse genetics competent unit of an influenza virus, For example, disclosed is a vector is named BacFluRG for delivery of at least a portion of influenza virus that when administered to a subject stimulates the subject's immune system to respond to the antigenic portions of the influenza virus.

Disclosed are methods and compositions for in vivo delivery of a pathogenic agent comprising a vector and a reverse genetics competent unit of a pathogenic agent, wherein the vector comprises bacmid, baculovirus expression system, synthetic vectors, or vectors known to those skilled in the art; wherein the pathogen comprises viral agents, bacterial agents and parasites; further comprising protein expression units and under the control of appropriate RNA promoters. As used herein, pathogenic agent or pathogen may be used interchangeably, but in the aspects disclosed herein, an infectious whole pathogen is not delivered in the compositions disclosed herein, but instead, the genome and/or proteins of a pathogen or pathogenic agent are provided to a cell. The cell may synthesize and assemble an entire pathogen from the genome and/or proteins encoded by the vector provided to the cell. Additionally, the vaccinated subject receiving the vector may later be challenged by a separate, whole pathogen to show vaccination protection provided by compositions and methods disclosed herein.

Additional advantages of the disclosed method and compositions will be set forth in part in the description which follows, and in part will be understood from the description, or can be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIG. 5 provides identification of recombinants: FIG. 5A-Modification of pFastΔplh donor vector. The PCR results and the sequence of the modified vector showed that the plh promoter had been removed. (SEQ ID NO:60-63 are shown top to bottom). FIG. 5B-Verification of Bacmid-P6 and Bacmid-HANA. Line 1-8 respected the PCR amplicons by the common flu primers for PB2, PB1, PA, HA, NP, NA, M, and NS (Table.1) FIG. 5C-Bacmid-P8LP and Bacmid-P8HP. Line 1-8 respected the PCR products by the primers PB2-1643F/2341R; PB1-1240F/2341R; PA-892F/2233R, HA-clvF/NS890R; NP-1116F/1565R; NA-1200F/1413R, M7-41F/1027R; and NS-474F/890R, respectively.

FIG. 8 provides a schematic representation for the construction of a bcmd-RGFlu vector: FIG. 8A shows the cloning of RG competent units (bi-directional RNA pol 1 and 2 promoters flanking a cDNA copy) of the internal gene segments of a given influenza virus strain and further modification with the incorporation of lambda phage attR recombination units flanking the thymidine kinase gene, pƏFP6attTK. FIG. 8B shows RG competent units for the HA and NA gene segments cloned into the pENTER-1A vector to generate the pE46 vector. FIG. 8C shows the plasmid pƏFP8 containing 8 RG influenza virus competent units.

FIG. 9 provides a schematic representation of de novo influenza virus synthesis from bcmd-RGF1u constructs.

FIG. 11 provides the results of studies showing the use of Bcmd-P8Ty04ts (H1N1$_{PR8}$) for protection of mice against lethal PR8 virus challenge. FIG. 11A shows the results of bcmd-P8Ty04ts (H1N1$_{PR8}$) or 8 µg of the corresponding plasmid RG transfected into co-cultured 293T/MDCK cells and FIG. 11B shows them transfected into co-cultured Vero cells. FIG. 11C shows survival data and FIG. 11D shows body weight changes over a 14 day period following challenge with 100 MLD$_{50}$ of PR8 virus administered intranasally 7 days after boost vaccination.

DETAILED DESCRIPTION

Figure 1:
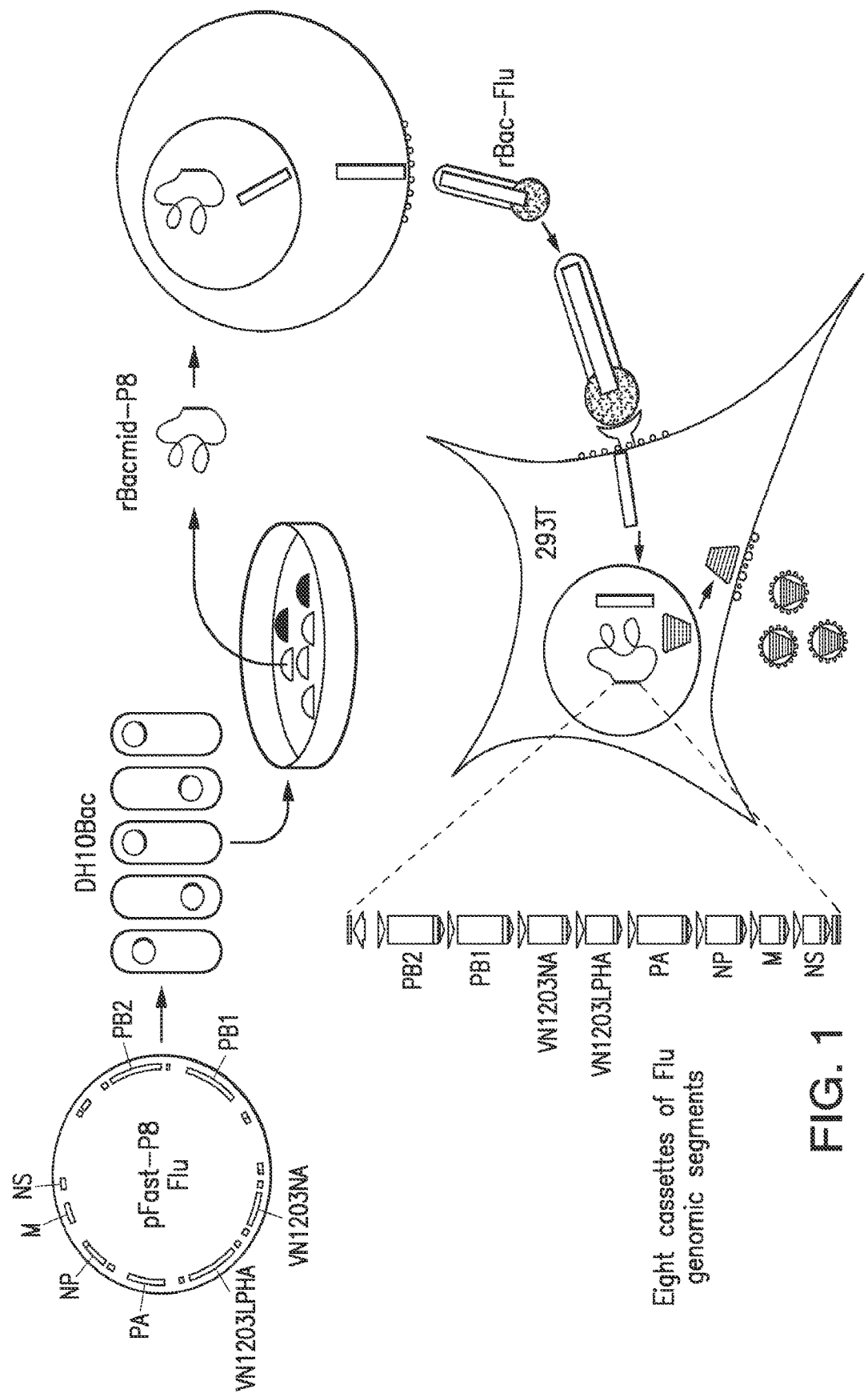
FIG. 1 provides a schematic showing the generation of a recombinant baculovirus transducer to carry influenza virus genome FIG. 2 provides a schematic showing construction of all the 8 internal segment cassettes of influenza virus in a single plasmid

The disclosed methods and compositions can be understood more readily by reference to the following detailed description of particular embodiments and the Example included therein and to the Figures and their previous and following description.

The present invention comprises compositions and methods for stimulating the immune system of a subject, such as a human or animal, by providing compositions comprising DNA constructs that express one or more desired antigens, such as pathogenic or oncogenic antigens, in the subject to stimulate an immune response by the subject. Methods and compositions disclosed herein comprise providing DNA constructs that express nucleic acid polymers that may, for example, be the genome or a portion of a genome of a pathogenic organism. Such a polynucleotide molecule may be a template for protein synthesis. Methods and compositions disclosed herein may be used for manipulating pathogenic agents or portions of pathogens to provide better vaccines, increased pathogenic protein or genome expression, and/or for producing pathogenic agent-containing vectors. The present invention further provides compositions and methods for manipulating influenza virus or portions of the influenza virus to provide in vivo vaccines.

Vaccination is the first line of defense against many pathogenic infections, especially influenza infections, yet vaccine production methods are slow, antiquated, and expensive to effectively reduce the infectious agent's burden during epidemic or pandemic periods. There is a great need for alternative vaccines and vaccination methods with a global scale impact. The methods and compositions described herein provide a novel approach for generating effective vaccines against infectious agents, including, but not limited to influenza infections. The methods described herein enable the generation of in vivo virus production, i.e. in vivo influenza virus production. Though influenza is provided as an example herein, the present invention contemplates that pathogenic agents other than influenza are comprised in the methods and compositions disclosed herein, and the invention is not to be limited by the disclosure herein. Those of skill in the art could perform the methods and compositions taught herein with such an understanding.

Type A Influenza (Flu) viruses, also known as influenza A viruses (IAVs), belong to the family Orthomyxoviridae and their genome consists of eight segments of single-stranded RNA of negative polarity [Webby R J, et al. (2007) Cur.r Top. Microbiol. Immunol. 315: 67-83; Yamanaka K, et al. (1991) Proc Natl Acad Sci USA 88:5369-5373; Lopez-Turiso J A, et al. (1990) Virus Res 16: 325-337.]. The virus has an envelope with a host-derived lipid bilayer and covered with about 500 projecting glycoprotein spikes with hemagglutinating and neuraminidase activities. These activities correspond to the two major surface viral glycoproteins: the hemagglutinin (HA) and neuraminidase (NA), present as homotrimers and homotetramers, respectively. Within the envelope, a matrix protein (M1) and a nucleocapsid (NP) protein protect the viral RNA (Lamb, 1989). The type designation (A, B, or C) is based upon the antigenic features of the M1 and NP proteins. Approximately half of the total genome encodes for the three viral polymerase proteins (segments 1, 2 and 3; (Palese et al, 1977). Segment 5 encodes the NP protein. The three-polymerase subunits (PB1, PB2, and PA), the NP and the vRNA are associated in virions and infected cells in the form of viral ribonucleoprotein particles (vRNPs). Segments 4 and 6 encode for the HA and NA genes, respectively. The two smallest segments (7 and 8) encode two genes each with overlapping reading frames, which are generated by splicing of the co-linear mRNA molecules (Lamb and Lai, 1980; Lamb and Lai, 1984; Lamb et al, 1981). In addition to M1, segment 7 encodes for the proton pump transmembrane protein (M2), which has ion channel activity and is embedded in the viral envelope. Segment 8 encodes for NS1, a nonstructural protein that blocks the host's antiviral response, and the nuclear export protein (NS2 or NEP) a structural component of the viral particle. NEP/NS2 interacts with the cellular export machinery and participates in the assembly of virus particles. Recently, NEP/NS2 has also been implicated in playing a role in the regulation of influenza virus transcription and replication. Thus, the eight RNA segments encode for 10-12 viral proteins, including two surface glycoproteins, HA and NA, M2, M1, NS2/NEP, NS1 and, in some influenza viruses (from an alternative translation start site in segment 1) the PB1-F2, an apoptosis modulatory protein [Arias C F, et al. (2009) Arch Med Res 40: 643-654; Zell R, (2006) Emerg Infect Dis 12: 1607-1608; author reply 1608-1609; Chen W, et al. (2001) Nat Med 7:1306-1312.]. Additional viral protein products include PB1-N40, derived from an alternative start site within the PB1 ORF, resulting in a protein product that lacks the first 39 aa of PB1, and PA-X, derived from the PA mRNA and consists of the N-terminal 191 aa of PA fused to 61 aa that result from +1 frameshifting [Jagger B W, et al. (2012) Science 337: 199-204; Yewdell J W, Ince W L (2012) Science 337: 164-165.].

DNA vaccines are undoubtedly the most cost-effective vaccines to produce. Despite their simplicity and solid safety history, DNA vaccination development has been hampered by its low immunogenicity in humans (Gurunathan et al. Annu Rev Immunol 18:927-974 (2000)). The inventors herein overcame the limitation in immunogenicity of DNA vaccines by providing alternative machinery capable of amplifying the antigen of interest. The inventors demonstrate the successful de novo generation of influenza viruses in vivo (mice) using a transfection-based inoculation method and a vector such as a baculovirus expression system or recombinant bacmid as delivery vehicle for the influenza virus RG clone. The present invention therefore enables the teaching of DNA vaccine development with enhanced antigen production in vivo.

In certain embodiments, the present invention comprises a vector comprising a reverse genetics competent unit. The vector may comprise any vector known to those skilled in the art, including but not limited to baculovirus expression vectors, bacmids, vaccinia virus, other large viruses, and synthetic vectors. A "reverse genetics competent unit" comprises portions of a pathogenic agent for synthesis of entire pathogens de novo or antigenic portions of a pathogenic agent from a nucleotide-based vector. In certain embodiments, the reverse genetics competent unit comprises portions of a pathogenic agent necessary for producing pathogens de novo from a nucleotide-based vector for infectious agents including but not limited to, poliovirus, Newcastle disease virus, influenza virus, and other agents such as those comprising positive sense and negative sense RNA viruses, bacterial pathogens and parasitic pathogens. Vectors of the present invention may encode at least a portion of genomes, proteins or peptides, that when expressed by the vector and or cell lead to the synthesis of an entire pathogen, or provide antigens to which a subject having an immune system may respond. The immune response may provide modulation of the immune response in the subject when the subject is subsequently challenged with the pathogen. A vector may comprise at least a portion of an oncogenic protein or antigen to which a subject having an immune system may respond. The immune response may provide modulation of the immune response in the subject when the subject is exposed to the oncogenic protein.

Baculoviruses (BVs) are powerful transducers of mammalian and avian cells. BVs have been approved by the FDA and are currently being evaluated for gene therapy in the treatment of cancer and other genetic diseases. Aspects of the present invention provide a new method for influenza vaccination that relies on the concept of in vivo reverse genetics, which is the concept of a "Trojan horse" approach in which a vector, such as a baculovirus vector, carries the necessary components for the generation of a live attenuated influenza virus (LAIV) in vivo (FIG. 1).

Methods of the present invention comprise synthesis of vectors. In aspects of the present invention, a modified donor plasmid, pFastΔplh (4648 bp) was developed for subcloning of the gene segments of influenza viruses. pFastΔplh is based on the donor plasmid pFastBac1™ (Bac-to-Bac® Baculovirus expression system, Invitrogen (Grand Island N.Y., USA)) and in which the polyhedrin promoter (plh) was removed. A polymerase chain reaction (PCR) was performed with using the pFastBac1 vector as the template and two synthetic primers (BamHI-Fwd and BamHI-Rev, see in Table. 1). The amplicon (4.4 kb) was treated with BamHI and ligated to generate pFastΔplh. The pFastΔplh vector was identified by sequencing with the primer DelPlh-Fwd and confirmed by digestion with BamHI, BssHII, SpeI, NotI, XbaI, XhoI, and KpnI (NEB) to make sure these enzymes do not digest the plasmid into more than one single fragment.

In aspects of the invention, a molecular cloning vector was constructed that included six internal gene segments of influenza A virus into the modified donor plasmid pFastΔplh according as described above. The vector, pΔFast-P6 (21.908 kb), contained the PB2, PB1, PA, NP, M, and NS gene segments of the influenza virus strain A/Puerto Rico/8/1934 (H1N1) (PR8) in pFastΔplh. The PR8 amplicons were amplified with specific primers spanning the CMV promoter and BGH polyA signal of pDP-PB2$_{PR8}$, pDP-PB1$_{PR8}$, pDP-PA$_{PR8}$, pDP-NP$_{PR8}$, pDP-M$_{PR8}$ and pDP-NS$_{PR8}$ plasmids, respectively.

An additional cloning vector, the Gateway cloning vector, comprises pΔFattTK-P6 (24.16 kb), wherein attR1/attR2 elements were introduced into the pΔFast-P6 plasmid according to the methodology described above. The attR elements were amplified from the BaculoDirect™ N-GST Linear DNA (linearized with Bsu36 I) in BaculoDirect™ N-Term expression kit by the primers SpeI-attR1F and SpeI-attR2R. To remove the lacZ box for reducing the insert size, two internal overlapping primers TkIERev and IEattR2F to separate the attR1-tk-pIE-1(0)-p10-lacZ-attR2 element into two parts were introduced. One was from attR1-Tk-pIE-1(0), another was only the attR2 sequence. Then, using overlapping PCR, the attR1-tk-pIE-1(0)-attR2 element were obtained. After being digested with SpeI, the amplicon was subcloned into pΔFast-P6 vector as above, and this recombinant vector was used for further studies.

An additional cloning vector, named the Enter vector, comprises pENTR-ΔH5N1 (8376 bp), was prepared according to the methodology described above. The first step was to amplify the PCR products from pDP-HA$_{VN1203}$, HA$_{ΔVN1203}$ and pDP-NA$_{VN1203}$ plasmids using BamHI-CMVF/NotI-BGHR and NotI-CMVF/XhoI-BGHR primers, separately. Notably, the polybasic cleavage site sequence (RERRRKKR; (SEQ ID NO:59) of HA$_{ΔVN1203}$ were substituted with RETR motif from the plasmid HA$_{vN1203}$. HA$_{ΔVN1203}$ was subcloned into pENTR-1A Dual vector (Invitrogen) and then the NA$_{VN1203}$ PCR product was cloned into pENTR-HA$_{ΔVN1203}$ to construct a Gateway Enter plasmid, pENTR-ΔH5N1.

Aspects of the present invention comprise a novel Gateway cloning strategy to subclone the HA and NA cassettes from a vaccine candidate into the pΔFattTK-P6 plasmid or Bacmid-attP6TK DNA. The final vectors include all the eight segments of reassortants. The pΔFast-P8LP vector is transposed into DH10Bac competent cells to obtain Bacmid-P8LP. A recombinant baculovirus rBac-P8LP (27.49 kb) carrying the genomic cDNA elements of ΔH5N1:6PR8 reassortant is disclosed herein. The recombinant viruses were infected into 293T/MDCK cells at a dose of 5 m.o.i or more. In experiments disclosed herein the ΔH5N1:6PR8 reassortants were rescued at 72 hpi (Table.4, 5).

Methods and compositions disclosed herein may comprise other known pathogens including other influenza viruses. See for example, the construction of H5N1, H9N2 and H3N2 virus (Table. 6). Other pathogens or portions of pathogenic agents may need to be cloned into sites of the vector that are suitable for use in the methods and compositions of the present invention.

In aspects, in vivo virus or pathogenic agent production comprises the use of bacmid DNAs. Disclosed herein are methods, that compared to the classical reverse genetics system, the "eight-in-one" bacmids (bcmd-RGFlu) showed higher efficiency of virus rescue in various cell types. Using a transfection-based inoculation (TBI) system, intranasal delivery in DBA/2J mice of bcmd-RGFlu plus 293T cells led to the generation of lethal PR8 virus in vivo. A prime-boost intranasal vaccination strategy using TBI in the context of a bcmd-RGFlu encoding a temperature sensitive H1N1 virus resulted in protection of mice against lethal challenge with the PR8 strain. The methods and compositions disclosed herein are useful for vaccination against infections such as those caused by influenza A or other pathogens by in vivo reverse genetics.

Disclosed herein are methods of in vivo synthesis of a vaccine, comprising, providing to at least one cell of a subject at least one vector comprising an exogenous DNA construct encoding at least a portion of a pathogenic agent or an oncogenic protein, wherein one or more antigenic peptides encoded by the DNA construct are expressed in the cell and stimulate an immune response in the subject to the pathogenic agent. A method may comprise wherein one or more copies of at least a portion of a genome of a pathogenic agent are expressed in the cell. A method may comprise wherein the DNA construct is a reverse genetics competent unit. A method may comprise wherein multiple copies of a pathogenic agent genome are expressed in the cell. A method may comprise wherein the vector further comprises a reverse genetics competent unit. A method may comprise wherein the vector comprises a bacmid, a baculovirus expression system, or a synthetic vector. A method may comprise wherein the pathogenic agent comprises a virus, a bacteria or a parasite. A method may comprise wherein the pathogenic agent comprises an orthomyxovirus. A method may comprise wherein the pathogenic agent comprises an influenza virus. A method may comprise wherein the vector comprises a recombinant baculovirus vector and a reverse genetics competent unit comprising influenza virus. A method may comprise wherein the vector comprises a bacmid and a reverse genetics competent unit of influenza A virus. A method may comprise wherein the vector comprises protein expression units and genome transcription units under the control of appropriate promoters. A method may further comprising protein expression units under the control of RNA pol II promoters and viral transcription units under the control of RNA pol I promoters. A method may comprise wherein live attenuated influenza vaccine is produced directly in vivo. A method may comprise providing the vector in a cell to the subject. A method may comprise wherein two vectors are provided, and one vector encodes surface antigens of the pathogenic agent. A method may comprise wherein two vectors are provided, and one vector encodes proteins for replication of the pathogenic agent.

Disclosed herein are compositions, for example, an influenza vaccine composition, comprising a bacmid vector comprising a reverse genetics competent unit of influenza virus, wherein the genome of influenza virus is expressed is a cell and one or more antigenic peptides of influenza are expressed in a cell. A composition may comprise wherein the composition is a pharmaceutical composition. A composition may comprise transducer enhancers or adjuvants. A composition may comprise wherein the composition is formulated to be administered via intranasal inoculation, intradermal inoculation, microneedle administration, subcutaneous administration, aerosol delivery, or intramuscular administration. A composition may comprise wherein the reverse genetics competent unit of influenza virus comprises PB2, PB1, PA, NP, M, and NS gene segments. A composition may comprise wherein the gene segments are from the influenza virus strain A/Puerto Rico/8/1934 (H1N1). A composition may comprise wherein the bacmid vector of the composition is the result of recombination between a bacmid vector encoding internal proteins of influenza and a bacmid vector comprising the HA and N proteins of influenza so that the bacmid vector of the composition encodes and expresses each of the proteins of influenza.

Disclosed herein are methods for modulating the immune system of a subject having an immune system. A method may comprise a method of immune stimulus from in vivo synthesis of a vaccine, comprising, providing to at least one cell of a subject at least one vector comprising an exogenous DNA construct encoding at least a portion of a pathogenic agent or an oncogenic protein, wherein one or more antigenic peptides encoded by the DNA construct are expressed in the cell and stimulate an immune response in the subject to the pathogenic agent. A method may comprise wherein one or more copies of a portion of a genome of the pathogenic agent are expressed in the cell. A method may comprise wherein the DNA construct is a reverse genetics competent unit. A method may comprise wherein multiple copies of the genome are expressed in the cell. A method may comprise wherein the vector further comprises a reverse genetics competent unit. A method may comprise wherein the vector comprises a bacmid, a baculovirus expression system, or a synthetic vector. A method may comprise wherein the pathogenic agent comprises a virus, a bacteria or a parasite. A method may comprise wherein the pathogenic agent comprises orthomyxovirus. A method may comprise wherein the pathogenic agent comprises influenza virus. A method may comprise wherein the vector comprises a recombinant baculovirus vector and a reverse genetics competent unit comprising influenza virus. A method may comprise wherein the vector comprises a bacmid and a reverse genetics competent unit of influenza A virus. A method may comprise wherein the vector comprises protein expression units and genome transcription units under the control of appropriate promoters.

A method may comprise protein expression units under the control of RNA pol II promoters and viral transcription units under the control of RNA pol I promoters. A method may comprise wherein live attenuated influenza vaccine is produced directly in vivo.

A method may comprise providing the vector in a cell to the subject. A method may comprise wherein a booster immunization of the vector disclosed herein is administered at least a second time to the subject. A method may comprise wherein a booster immunization of a killed or attenuated vaccine of the same pathogenic agent is administered at least a second time to the subject.

Methods of Immunizing or Inducing Protective Immunity

Disclosed are methods of immunizing or inducing a protective immune response in a subject against an infectious agent such as influenza virus by administering an effective amount of a vector comprising a reverse genetics competent unit of a pathogen. In certain embodiments the vector may comprise a baculovirus expression system, or a bacmid, and the pathogen may comprise a virus, bacteria or parasite.

In some aspects, administering an effective amount of a vector comprising a reverse genetics competent unit of a pathogen includes administering a vector wherein the reverse genetics competent unit corresponds to influenza virus. In some aspects additional components such as protein expression units and viral transcription units under the control of appropriate RNA promoters are included. In some embodiments, the protein expression units under the control of RNA pol II promoters and viral transcription units under the control of RNA pol I promoters are included.

Methods of Increasing Viral Protein/Viral Particle Production

Disclosed are methods of increasing infectious agent protein production by administering to a subject an effective amount of a delivery vector comprising comprising a vector and a reverse genetics competent unit of a pathogen. In certain embodiments the vector comprises bacmid, baculovirus expression system, and synthetic vectors. In certain embodiments the pathogen comprises viral agents, bacterial agents and parasites. In certain other embodiments the virus comprises an orthomyxovirus, such an influenza virus.

Disclosed are methods of increasing influenza viral particle production by transfecting cells with a vector that encodes the gene sequences for hemagglutinin (HA), neuraminidase (NA), matrix (M1), nucleocapsid (NP), NS1 and NS2.

A construct that comprises the gene sequences can be a plasmid or an amplicon. The gene sequences for other influenza gene, including but not limited to, HA, NA, M1, NP, NS1 and NS2, may be provided on plasmids or amplicons.

Administration

Delivery vehicles, vectors, vaccines, compositions, constructs and viruses of the present invention disclosed herein can be for administration by oral, parenteral (intramuscular, intraperitoneal, intravenous (IV) or subcutaneous injection), transdermal (either passively or using iontophoresis or electroporation), or transmucosal (nasal, vaginal, rectal, or sublingual) routes of administration or using bioerodible inserts and can be formulated in unit dosage forms appropriate for each route of administration.

Administration to subjects may involve the vector, construct, virus or vaccine of interest to be formulated into a pharmaceutically acceptable carrier. Pharmaceutically acceptable carriers are well known in the art.

Administration of the disclosed compositions can be accomplished by any acceptable method which allows an effective amount of the pathogen, i.e. influenza virus to achieve its intended effects. The particular mode selected will depend upon factors such as the particular formulation and the dosage required to induce an effective response.

Kits

Delivery vectors, vaccines, compositions, constructs and viruses described herein as well as other materials can be packaged together in any suitable combination as a kit useful for performing, or aiding in the performance of, the disclosed method. It is useful if the kit components in a given kit are designed and adapted for use together in the disclosed method. For example disclosed are kits for producing amplicons, the kit comprising amplification primers. The kits also can contain nucleic acid sequences for some or all influenza genes, portions of sequences, and/or regulatory sequences.

A. Definitions

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a recombinant influenza virus" includes a plurality of such viruses, reference to "the nucleic acid sequence" is a reference to one or more nucleic acid sequences and equivalents thereof known to those skilled in the art, and so forth.

As used herein the term "effective amount" or means a dosage sufficient to provide the desired pharmacologic and/or physiologic effect. For example, an effective amount of a recombinant influenza virus can increase viral protein production, increase viral particle production, and increase a subject's immune response. The precise dosage will vary according to a variety of factors such as subject-dependent variables (e.g., age, immune system health, etc.).

The term "exogenous sequence" refers to a sequence other than a sequence found in the host. For example, a recombinant influenza virus with a rearranged genome that contains an exogenous sequence means that the exogenous sequence is a sequence other than a sequence found in the host influenza virus. The exogenous sequence can be from a different strain of influenza virus.

The term "operably linked" refers to nucleic acid sequences placed into a functional relationship with another nucleic acid sequence. For example, a promoter is operably linked to a coding sequence if it affects the transcription of the sequence. Generally, "operably linked" means that the nucleic acid sequences being linked are contiguous and in reading frame. With respect to a rearranged viral genome segment having NS1 operably linked to an exogenous sequence means that expression of the NS1 sequence results in expression of the exogenous sequence.

The term "rearranged viral genome" refers to a viral genome that has been altered or rearranged so that at least one nucleic acid sequence is in a different order from that of the wild type sequence. A rearranged viral genome can include one or more rearranged viral genome segments.

The term "subject" refers to a mammal, including, but not limited to, humans, rodents such as mice and rats, other laboratory animals, cells, and cell lines.

"Optional" or "optionally" means that the subsequently described event, circumstance, or material may or may not occur or be present, and that the description includes instances where the event, circumstance, or material occurs or is present and instances where it does not occur or is not present.

As used herein the term "modulate" is meant to mean to alter, by increasing or decreasing. For example, disclosed herein are methods of using vectors comprising an exogenous DNA construct to increase viral production.

Ranges can be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

Those skilled in the art will recognize, or be able to ascertain using no more than routine experimentation, many equivalents to the specific embodiments of the method and compositions described herein. Such equivalents are intended to be encompassed by the following claims.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

EXAMPLES

Example 1

Subcloning Strategies
(A) Construction of pΔFast-P6 Donor Plasmid

The recombinant plasmid pΔFast-P1 was constructed by subcloning the PB2 amplicon in the pDP-PB2 plasmid (from CMV promoter to BGH polyA with the primers BamHI-CMVF and BssHII-BGHR) into pFastΔplh by treatment with BamHI and BssHII. The ligation reaction was followed by Quick Ligation kit (New England Biolabs, Ipswich, Mass.). The ligation product was put at 4° C. overnight, and then transformed into One Shot® TOP10 Chemically Competent E. coli (Invitrogen). The positive clones were identified by PCR with the primers PB2-1643F/Ba-PB2-2341R using GoTaq® Green Master Mix (Promega), and sequenced by the SVpA-Rev primer (Table. 1). The recombinant plasmid was designated pΔFast-P1.

To subclone PB1 into the downstream of PB2, the PB1 amplicon in the pDP-PB1 plasmid was amplified with the BssHII-CMVF and SpeI-BGHR primers by Phusion high-fidelity PCR master mix with GC Buffer (NEB). The reaction and the further steps were similar to that of the pΔFast-P1 above. The positive clones were identified by PCR with PB1-1240F/Bm-PB1-2341R and sequenced by the SVpA-Rev primer (Table. 1). The recombinant plasmid was designated pΔFast-P2. To subclone PA into the downstream of PB2 and PB1, the PA amplicon in the pDP-PA plasmid was amplified with the SpeI-CMVF and NotI-BGHR primers. The ligation reaction was driven by a DNA Ligation kit for long fragments (Clontech and Takara) at 16 C overnight. Here, we used XL10-Gold® Chemically Competent E. coli (Strategene) to transform the ligation product, which contained repeat elements to avoid the recombinance. The positive clones were identified by PCR with PA-892F/Bm-PA-2233R and sequenced by the SVpA-Rev primer (Table. 1). The recombinant plasmid was designated pΔFast-P3. To subclone NP, M and NS into the pΔFast-P3, we firstly subcloned the NP, M and NS in one ligation reaction into pFastΔplh vector to avoid the difficulties in the further ligation and transformation processes. In this case, NP from pDP-NP, M from pDP-M, and NS from pDP-NS were separately amplified with the primers NotI-CMVF/XbaI-BGHR (NP), XbaI-CMVF/XhoI-BGHR (M) and XhoI-CMVF/KpnI-BGHR (NS). The three PCR amplicons were equally added in the ligation reaction, and ligated with the pFastΔplh donor vector digested with NotI and KpnI, followed by the Quick ligation kit at 4° C. overnight. The products were transformed into XL10-Gold® Chemically Competent *E. coli*. The positive clones were identified by three PCR reactions, separately with NP-892F/Bm-NP-2233R for NP, with M-741F/Bm-M-1027R for M, NS-477F/Bm-NS-890R for NS, and sequenced by the SVpA-Rev primer. The recombinant plasmid was designated pΔFast-NPMNS. To subclone NPMNS fragment into the MCS of pΔFast-P3 vector, the pΔFast-NPMNS plasmid was digested with NotI and KpnI, purified and ligated with pΔFast-P3 by the DNA Ligation kit for long fragments at 16° C. overnight. The products were transformed into MAX Efficiency® Stbl3 competent cells (Invitrogen). The positive clones were identified by six PCR reactions, separately with all the primers above and sequenced by the SVpA-Rev primer. The recombinant plasmid was designated pΔFast-P6.

To construct $HA_{PR8}$ and $NA_{PR8}$ expression elements into pFastΔplh vector, the $HA_{PR8}$ amplicon from pdmH1N1 virus was acquired with the primers BssHII-CMVF and XbaI-BGHR using pDP-$HA_{PR8}$ as templates, and the $NA_{PR8}$ amplicon was amplified with the primers XbaI-CMVF and KpnI-BGHR using pDP-$NA_{PR8}$ as templates, ant then the two amplicons were equally added with pFastΔplh donor vector, which had been digested with BssHI and KpnI.

In one ligation reaction, the ligation and transformation conditions were similar with the subcloning of pBac-NPMNS. The positive clones were identified by two PCR reactions, separately with HA-760F/Bm-NS-890R for $HA_{PR8}$, with NA-788F/Ba-NA-1413R for $NA_{PR8}$, and sequenced by the SVpA-Rev primer. The recombinant plasmid was designated pΔFast-H1N1$_{PR8}$.

TABLE 1

Primer Sets In This Study

| Primer Name | Sequence (5'-3') |
|---|---|
| BamHI-Fwd | ATTCATACCGTCCCACCATCG (SEQ ID NO: 1) |
| BamHI-Rev | CAGGATCCCTATTAATATTCCGGAGT (SEQ ID NO: 2) |
| DelPlh-Fwd | ACTCCGGAATATTAATAG (SEQ ID NO: 3) |
| SVpA-Rev | CTACAAATGTGGTATGGCTG (SEQ ID NO: 4) |
| BamHI-CMVF | ATCGGATCCAGGGCGACACGGAAATGTTGAA (SEQ ID NO: 5) |
| BssHII-BGHR | AATGCGCGCTGGCCGATTCATTAATGCAGCTG (SEQ ID NO: 6) |
| BssHII-CMVF | AATGCGCGCAGGGCGACACGGAAATGTTGAA (SEQ ID NO: 7) |
| SpeI-BGHR | ATCACTAGTTGGCCGATTCATTAATGCAGCTG (SEQ ID NO: 8) |
| SpeI-CMVF | ATCACTAGTAGGGCGACACGGAAATGTTGAA (SEQ ID NO: 9) |
| NotI-BGHR | ATAGCGGCCGCTGGCCGATTCATTAATGCAGCTG (SEQ ID NO: 10) |
| NotI-CMVF | ATAGCGGCCGCAGGGCGACACGGAAATGTTGAA (SEQ ID NO: 11) |
| XbaI-BGHR | CATTCTAGATGGCCGATTCATTAATGCAGCTG (SEQ ID NO: 12) |
| XbaI-CMVF | CATTCTAGAAGGGCGACACGGAAATGTTGAA (SEQ ID NO: 13) |

TABLE 1-continued

Primer Sets In This Study

| Primer Name | Sequence (5'-3') |
|---|---|
| XhoI-BGHR | AATCTCGAGTGGCCGATTCATTAATGCAGCTG (SEQ ID NO: 14) |
| XhoI-CMVF | AATCTCGAGAGGGCGACACGGAAATGTTGAA (SEQ ID NO: 15) |
| KpnI-BGHR | ATAGGTACCTGGCCGATTCATTAATGCAGCTG (SEQ ID NO: 16) |
| SpeI-attR1F | CTT ACTAGT ACAAGTTTGTACAAAAAAGCTG (SEQ ID NO: 17) |
| SpeI-attR2R | CAT ACTAGT ACCACTTTGTACAAGAAAGCTG (SEQ ID NO: 18) |
| RsrII-attR1-Fwd | TATcggtccgACAAGTTTGTACAAAAAAGCTG (SEQ ID NO: 19) |
| RsrII-attR2-Rev | TATcggtccgACCACTTTGTACAAGAAAGCTG (SEQ ID NO: 20) |
| TkIERev | TTGTCGCTGTACGCGGGCAAACCT (SEQ ID NO: 21) |
| IEattR2F | AGGTTTGCCCGCGTACAGCGACAA CATAGTGACTGGATATGTTG (SEQ ID NO: 22) |
| NheI-p10-F | ATAGCTAGCCCGGGACCTTTAATTCAAC (SEQ ID NO: 23) |
| SalI-p10-R | AGAGTCGACCAGTACTCCGGTCTCCTTTGATTG TAAATAAAATG (SEQ ID NO: 24) |
| AarI-pDP-F | TATTCGTCTCAGGGAATATGCAGGTGAAAAACA TATTCTC (SEQ ID NO: 25) |
| AarI-pDP-R | ATATCGTCTCGTATTCTAGGCAGGTGGGAGAAA AAAATC (SEQ ID NO: 26) |
| Entr-M-F | CGTATTTCGACTCGCTCAGG (SEQ ID NO: 27) |
| Entr-M-R | CCTGAGCGAGTCGAAATACG (SEQ ID NO: 28) |
| Seq-attTK-R | GTTTTCCGTAGAATCGAGAC (SEQ ID NO: 29) |
| pENTR-Seq | GTAACATCAGAGATTTTGAGACAC (SEQ ID NO: 30) |
| Uni12 | AGCAAAAGCAGG (SEQ ID NO: 31) |
| Ba-PB2-1 | TATTGGTCTCAGGGAGCAAAAGCAGGTC (SEQ ID NO: 32) |
| Ba-PB2-2341R | ATATGGTCTCGTATTAGTAGAAACAAGGGTCGTTT (SEQ ID NO: 33) |
| Bm-PB1-1 | TATTCGTCTCAGGGAGCAAAAGCAGGCA (SEQ ID NO: 34) |
| Bm-PB1-2341R | ATATCGTCTCGTATTAGTAGAAACAAGGGCATTT (SEQ ID NO: 35) |
| Bm-PA-1 | TATTCGTCTCAGGGAGCAAAAGCAGGTAC (SEQ ID NO: 36) |
| Bm-PA-2233R | ATATCGTCTCGTATTAGTAGAAACAAGGGTACTT (SEQ ID NO: 37) |
| Bm-HA-1 | TATTCGTCTCAGGGAGCAAAAGCAGGGG (SEQ ID NO: 38) |

TABLE 1-continued

Primer Sets In This Study

| Primer Name | Sequence (5'-3') |
|---|---|
| Bm-NS-890R | ATATCGTCTCGTATTAGTAGAAACAAGGGTGTTTT (SEQ ID NO: 39) |
| Bm-NP-1 | TATTCGTCTCAGGGAGCAAAAGCAGGGTA (SEQ ID NO: 40) |
| Bm-NP-1565R | ATATCGTCTCGTATTAGTAGAAACAAGGGTATT TTTT (SEQ ID NO: 41) |
| Ba-NA-1 | TATTGGTCTCAGGGAGCAAAAGCAGGAGT (SEQ ID NO: 42) |
| Ba-NA-1413R | ATATGGTCTCGTATTAGTAGAAACAAGGGAGTT TTTT (SEQ ID NO: 43) |
| Bm-M-1 | TATTCGTCTCAGGGAGCAAAAGCAGGTAG (SEQ ID NO: 44) |
| Bm-M-1027R | ATATCGTCTCGTATTAGTAGAAACAAGGGTAGT TTTT (SEQ ID NO: 45) |
| Bm-NS-1 | TATTCGTCTCAGGGAGCAAAAGCAGGGTG (SEQ ID NO: 46) |
| PB2-1643F | TCAATGATGTGGGAGATTAA (SEQ ID NO: 47) |
| PB1-1240F | GGAATGATGATGGGCATGTT (SEQ ID NO: 48) |
| PA-892 F | TTAAGCATTGAGGACCCAAGTCA (SEQ ID NO: 49) |
| HA-760F | TGAACTATTACTGGACCTTGC (SEQ ID NO: 50) |
| NP-1116F | GCTTTCCACTAGAGGAGTTC (SEQ ID NO: 51) |
| NA-788F | CAAGATCGAAAAGGGGAAGGTTAC (SEQ ID NO: 52) |
| M-741F | CCTATCAGAAACGAATGGGGG (SEQ ID NO: 53) |
| NS-474F | GGGCTTTCACCGAAGAGGGAG (SEQ ID NO: 54) |
| IndoH5-clvF | ACAGCCCTCAA ACTGAAACTAGA GGACTATTTGGAGCTATAG (SEQ ID NO: 55) |
| NA-1200F | AGGATATAGCGGGAGTTTTGT (SEQ ID NO: 56) |
| BamHI-EGFP-F | ATTGGATCCACCATGGTGAGCAAG (SEQ ID NO: 57) |
| EcoRI-EGFP-R | ATCGAATTCTTACTTGTACAGCTCGT (SEQ ID NO: 58) |

(B) Modification of pΔFast-P6 Plasmid with the attR-TK Element

To obtain a common recombinant baculovirus vector for flu viruses subtypes, we introduced the truncated attR1/attR2 elements into the pΔFast-P6 plasmid, which contains the 6 internal genes of the flu vaccine backbone PR8 virus. First, to amplify the elements from the BaculoDirect™ N-GST Linear DNA (linearized with Bsu36 I) in Baculo-Direct™ N-Term expression kit, the primers SpeI-attR1F and SpeI-attR2R were used to amplify the full size of the fragment between attR1 and truncated attR2 (attR1-tk-pIE (0)-p10-lacZ-attR2). To delete the lacZ box, we introduced two internal overlapping primers TkIERev and IEattR2F to separate the elements, and then amplified the attR1-Tk-pIE-1(0)-attR2 amplicon by overlapping PCR with the primers SpeI-attR1F and SpeI-attR2R. Second, the fragments were ligated into the single SpeI site of pΔFast-P6 plasmid using T4 DNA ligase (NEB) and then the ligation product was transformed into One Shot® ccdB Survival™ 2 T1R competent cells (Invitrogen). The positive clones were identified by seven PCR reactions, separately with all the primers above and sequenced by the SeqattTK primer (Table. 1). The recombinant plasmid was designated pΔFattP6TK, which was described in the supplementary information.

(C) Construction of HA and NA Dual-Expression Box into the Gateway Enter Vector

To obtain the HA and NA expression elements inserted into the linear 6 internal segments of PR8 genome, based on Gateway strategy, we introduced them into between the attL1 and attL2 sequences in pENTR-1A vector to exchange the HA and NA elements from vaccine candidates with the Thymidine kinase (TK) expression box from the pΔFattP6TK plasmid. We took $HA_{VN1203}$, $HA_{\Delta VN1203}$ and $NA_{VN1203}$ for proving our strategies. The first step was to amplify the PCR products from pDP-$HA_{VN1203}$, $HA_{\Delta VN1203}$ and pDP-$NA_{VN1203}$ plasmids using BamHI-CMVF/NotI-BGHR and NotI-CMVF/XhoI-BGHR primers, separately. Notably, the polybasic cleavage site sequence (RE-RRRKKR; SEQ ID NO:59) of $HA_{\Delta VN1203}$ were substituted with RETR motif from the plasmid $HA_{VN1203}$. $HA_{\Delta VN1203}$ was subcloned into pENTR-1A vector using BamHI and NoI sites. The recombinant plasmid was designated as pENTR-$HA_{\Delta VN1203}$ or pENTR-$HA_{VN1203}$ and then the $NA_{VN1203}$ PCR product was sublconed into the NoI and XhoI sites of pENTR-$HA_{\Delta VN1203}$ to construct the gateway enter plasmid: pENTR-ΔH5N1 and pENTR-H5N1. The positive clones were identified by PCR with H5N1 HA and NA primer pairs (IndoH5 Clv-F/Bm-NS890R; NA-1200F/Ba-NA 1413R) and sequenced by the SVpA-Rev primer (Table. 1).

(D) LR Gateway Reaction to Generate the Complete Genome of Flu Virus

Figure 2:
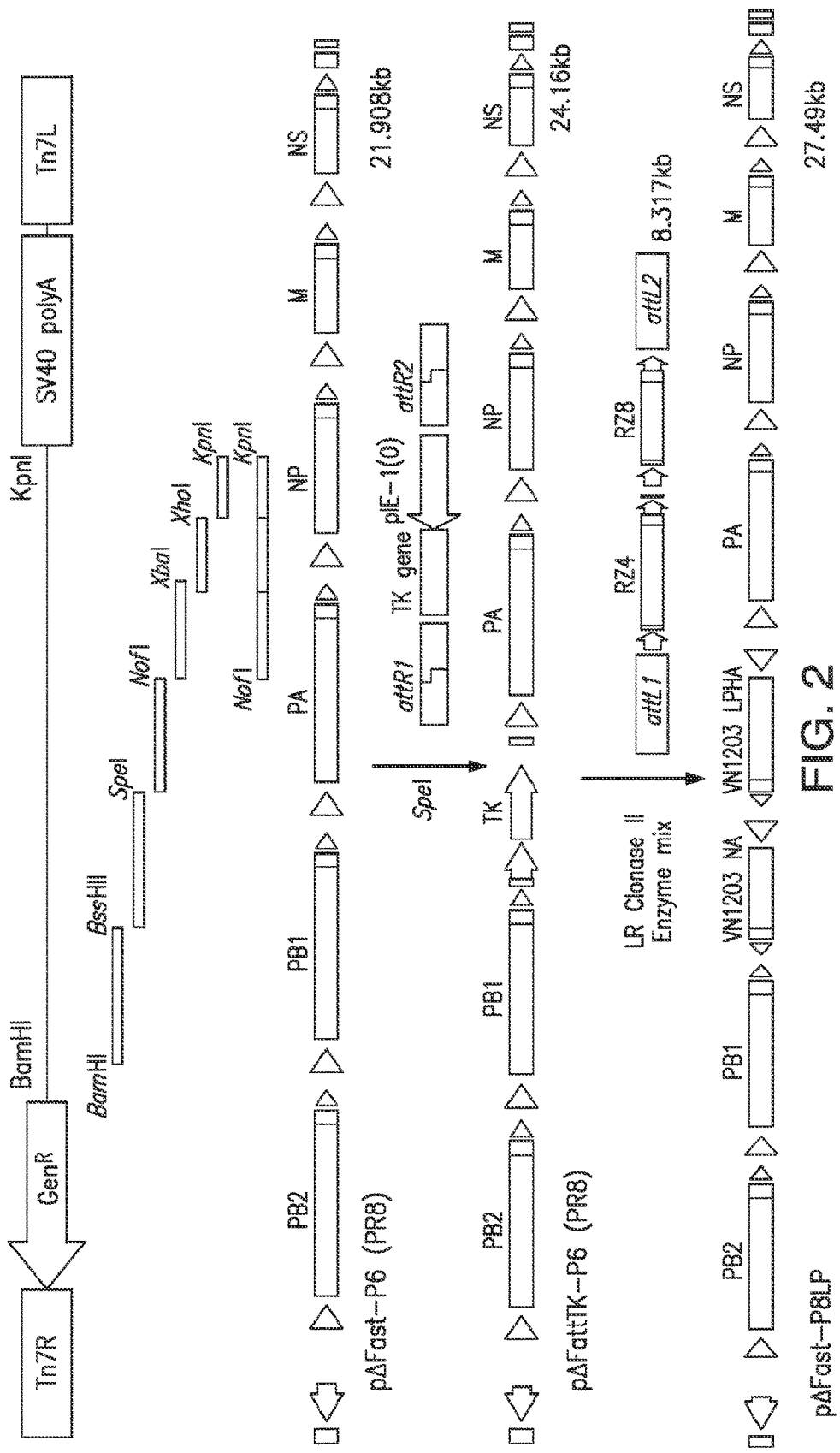
Figure 3:
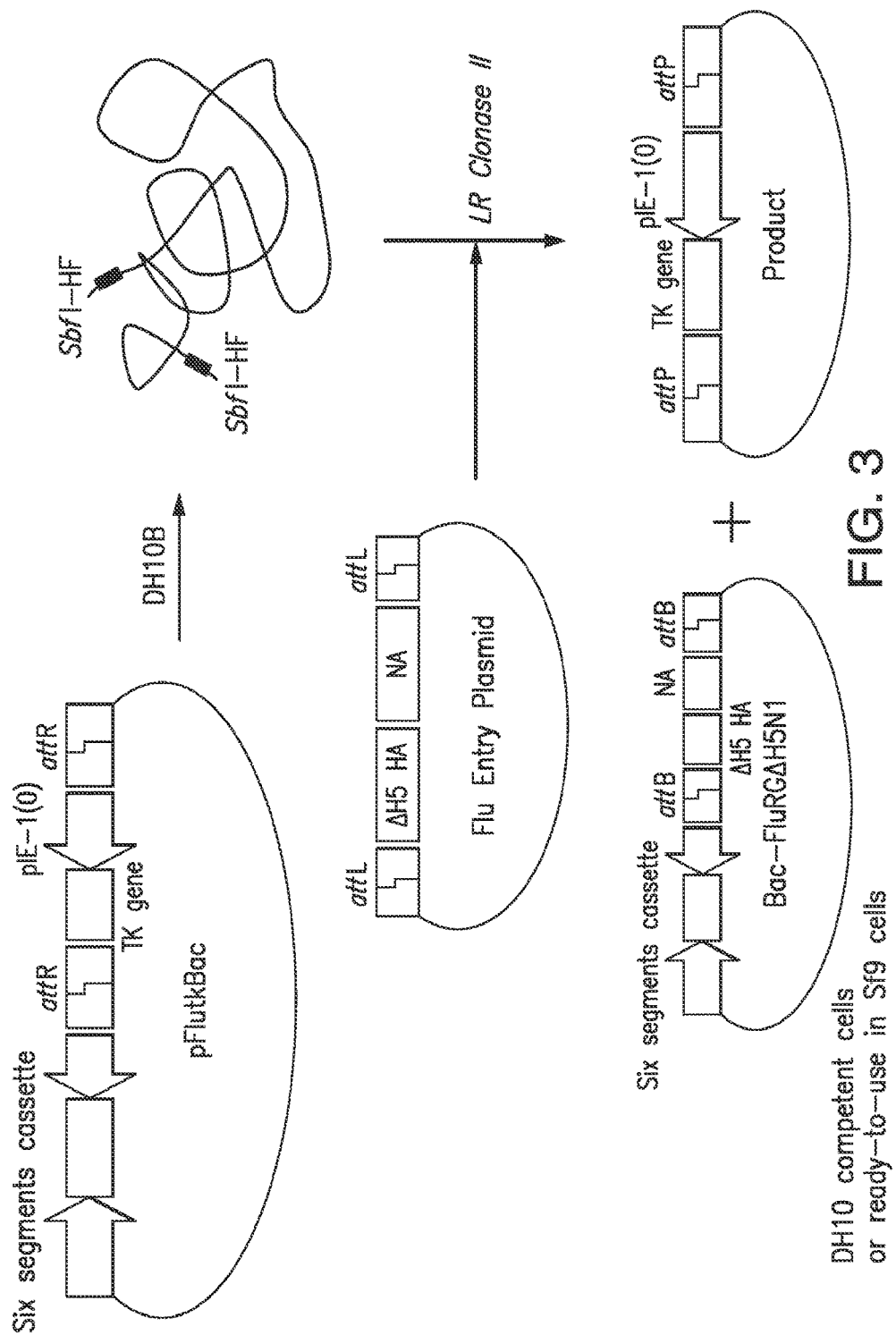
FIG. 3 shows construction of all the 8 internal segment cassettes of influenza virus in a single Bacmid.

To subclone HA and NA into the 6 internal gene cassettes, we introduced Gateway® LR cloning strategy to obtain the complete genome of influenza virus. Here, the LR Gateway cloning reaction included the circular pΔFattP6TK (100 ng) or linear Bacmid-P6attTK, pENTR-ΔH5N1 or pENTR-H5N1 (1 µg), Clonase™ II Enzyme Mix (4 µL) to a final volume of 20 µL in TE buffer (pH 8.0). For the strategy 1 on the circular pΔFattP6TK, the reaction maintained at 25° C. for 18 h. The final products were transformed into One Shot® ccdB Survival™ 2 T1R competent cells selected in 1.2% LB plates containing Amplicilin (100 µg/mL). Compared by different colonial size, the smaller clones were picked for PCR verification with the 8 primer pairs. The final plasmids are designated as pΔFast-P8LP and pΔFast-P8HP, respectively (FIG. 2). For the strategy 2 on the linear Bacmid-P6attTK (See in part 3), the final products were transformed into One Shot® ccdB Survival™ 2 T1R competent cells selected in 1.2% LB plates containing Bluo-gal (Sigma-Aldrich, St. Louis, Mo.), Isopropylthio-β-galactoside (IPTG) (Sigma), Gentamicin (Sigma), Kanamycin (Sigma), Tetracycline hydrochloride (Sigma) (FIG. 3). The final positive Bacmids were ready to use in Sf9 transfection.

Example 2

Identification of Activities of the Recombinant Plasmids

Figure 4:
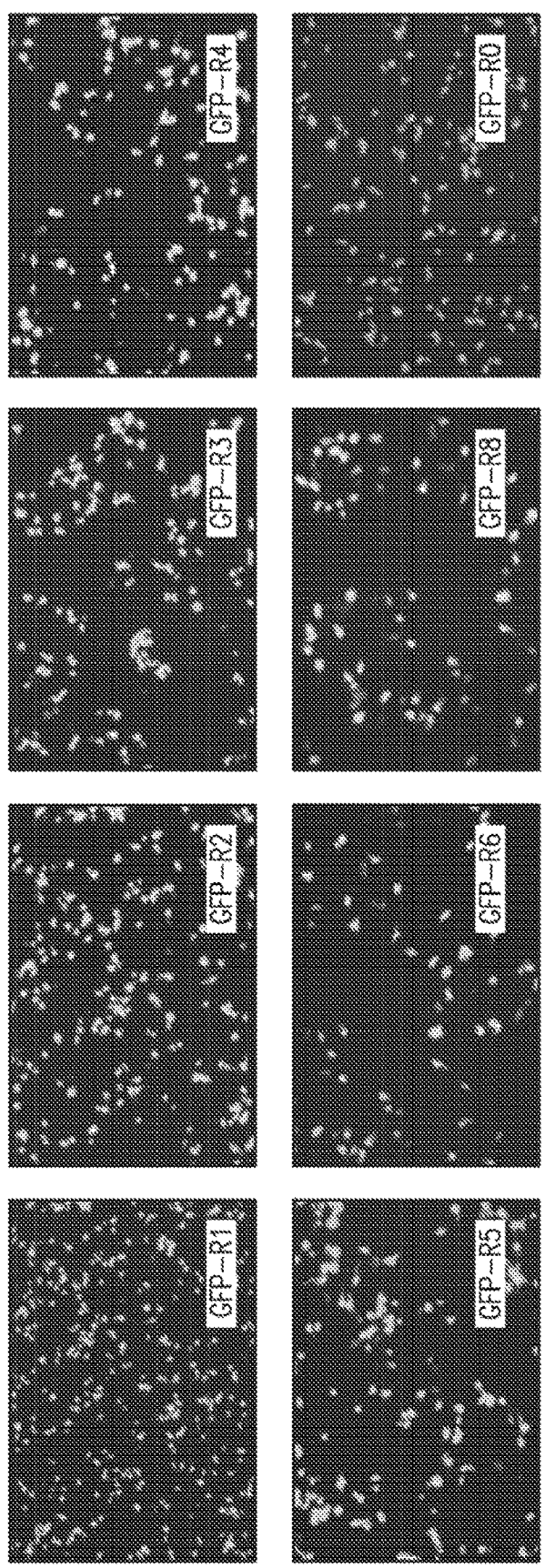
FIG. 4 provides identification of recombinant plasmids by EGFP reporter system.

Before following the each further step, the pHW-EGFP reporter plasmid was driven and expressed under the control of the constructed plasmids, including pΔFast-P1, pΔFast-P2, pΔFast-P3, pΔFast-P4, pΔFast-P5, pΔFast-P6, pΔFast-H1N1$_{PR8}$, pΔFattP6TK, pΔFast-P8LP, ΔFast-P8HP, pENTR-H5N1, and pENTR-AH5N1. The transfection groups were shown in the Table.2. The high pathogenic H5N1 reassortants were rescued in BSL-3 lab followed by SOPs of Biosafety protocols in BSL-3 lab of University of Maryland. The results are shown in FIG. 4.

TABLE 2

Identification of plasmids by EGFP reporter assay and virus rescue with recombinant plasmids or bacmids

| No. | Groups ID | Plasmids/Bacmids | The rest helper plasmids | Positive (+/−) or titer (TICD$_{50}$/mL) |
|---|---|---|---|---|
| 1 | GFP-R1 | pΔFast-P1 | pcDNA774PB1, pcDNA787PA, pcDNA693NP | +* |
| 2 | GFP-R2 | pΔFast-P2 | pcDNA787PA, pcDNA693NP | + |
| 3 | GFP-R3 | pΔFast-P3 | pcDNA693NP | + |
| 4 | GFP-R4 | pΔFast-P4 | / | + |
| 5 | GFP-R5 | pΔFast-P5 | / | + |
| 6 | GFP-R6 | pΔFast-P6 | / | + |
| 7 | GFP-R8 | pΔFast-P8LP | / | + |
| 8 | GFP-R0 | pΔFastDelplh | pcDNA762, pcDNA774, pcDNA787, pcDNA693 | + |
| 9 | RG-PR1 | pΔFast-P1 | pDP-PB1, PA, HA, NA, NP, M, NS | + |
| 10 | RG-PR2 | pΔFast-P2 | pDP-PA, HA, NA, NP, M, NS | + |
| 11 | RG-PR3 | pΔFast-P3 | pDP-HA, NA, NP, M, NS | + |
| 12 | RG-PR4 | pΔFast-P4 | pDP-HA, NA, M, NS | + |
| 13 | RG-PR5 | pΔFast-P5 | pDP-HA, NA, NS | + |
| 14 | RG-PR6 | pΔFast-P6 | pDP-HA, NA | + |
| 15 | RG-PR8 | pΔFast-P8LP | / | + |
| 16 | RG-PR8H | pΔFast-P8HP | / | + |
| 17 | RG-PR0 | pΔFastDelplh | pDP-PB2, PB1, PA, NP, M, NS, HA (VN1203), NA (VN1203) | + |
| 18 | RG-Bac1 | Bacmid-P6 + Bacmid-HANA | / | 1.58 × 10$^3$ |
| 19 | RG-Bac2 | Bacmid-P6 | / | − |
| 20 | RG-Bac3 | Bacmid-P8LP (LPH5N1) | / | 1.58 × 10$^b$ |
| 21 | RG-Bac4 | Bacmid-P8HP (HPH5N1) | / | 1.58 × 10$^{6\ \#}$ |
| 22 | RG-Bac6 | rDH10 | / | − |

*GFP-R: Polymerase activity assay with the pHW-GFP reporter plasmid;
Bacmid-P8HP DNA was transfected and the virus was rescued without TPCK-trypsin solution in BSL-3 lab.

Example 3

Transposition and Transfection

Transposition of pΔFast-P6, pΔFast-H1N1$_{PR8}$, pΔFast-P6attTK, pΔFast-P8LP and pΔFast-P8HP into MAX Efficiency® DH10Bac™ Competent *E. coli* (Invitrogen) was selected in 1.2% LB plates containing Bluo-gal, IPTG, Gentamicin, Kanamycin, Tetracycline hydrochloride according to the instructions for the BactoBac baculovirus expression system. 3 times after negative pressure by antibiotics, the white clones were picked and Bacmid DNAs were extracted and identified by the PCR reactions with the 8 primer sets described in the supplementary informations. The positive recombinant Bacmids were designated as Bacmid-P6, Bacmid-P6attTK, Bacmid-H1N1$_{PR8}$, Bacmid-P8HP, and rBacmid-P8LP, separately, and then transfected into Sf9 insect cells with Cellfectin® II Reagent (Invitrogen). The baculoviruses, respectively designated as rBacP6, rBacH1N1 prs, rBacP8LP and rBacP8HP, were passaged by infecting Sf9 cells at a multiplicity of infection (M.O.I) of 0.1, harvested 4 days postinfection, and titrated by the end-point dilution method.

Example 4

Purification of Recombinant Baculoviruses

The recombinant baculoviruses were produced by infecting Sf9 cells at an MOI of 0.1. Supernatants were collected 4 d after infection and were clarified by centrifugation at 3000 g for 30 min at 4° C. to remove cell debris. Viral particles were precipitated via ultracentrifugation (25,000 rpm using a Sorvall SW42 rotor) for 2.5 h at 4° C. The pellets were subsequently resuspended in sterile phosphate-buffered saline (PBS) and stored at 4° C. The viral titer was determined using GP64-FITC mAb and was expressed as infectious units per milliliter (ifu/mL).

Example 5

Sequence Analysis

Figure 5D:
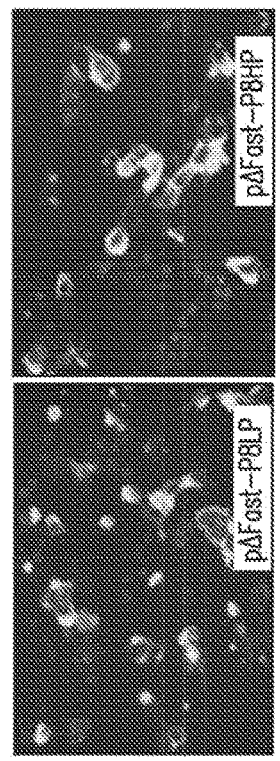
FIG. 5D-Western-blotting analysis of pΔFast-P6 with PB2, PB1, NP and NS antibodies.
Figure 5E:
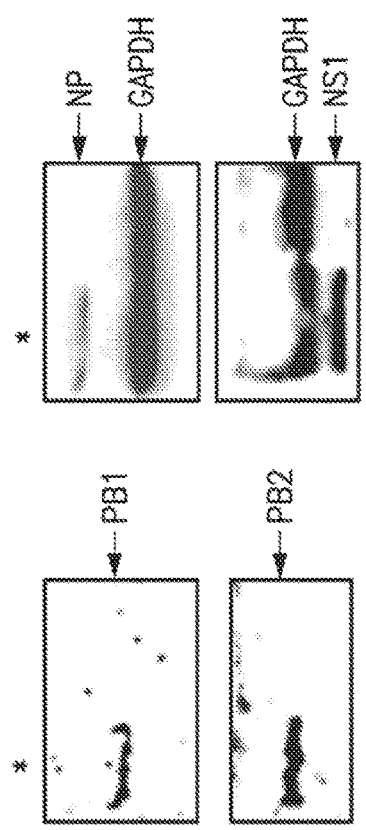
FIG. 5E-IF assay of pΔFast-P8LP and pΔFast-P8HP transfected on 293T cells with mAb DPJY01 against HA of H5N1 virus.
Figure 5F:
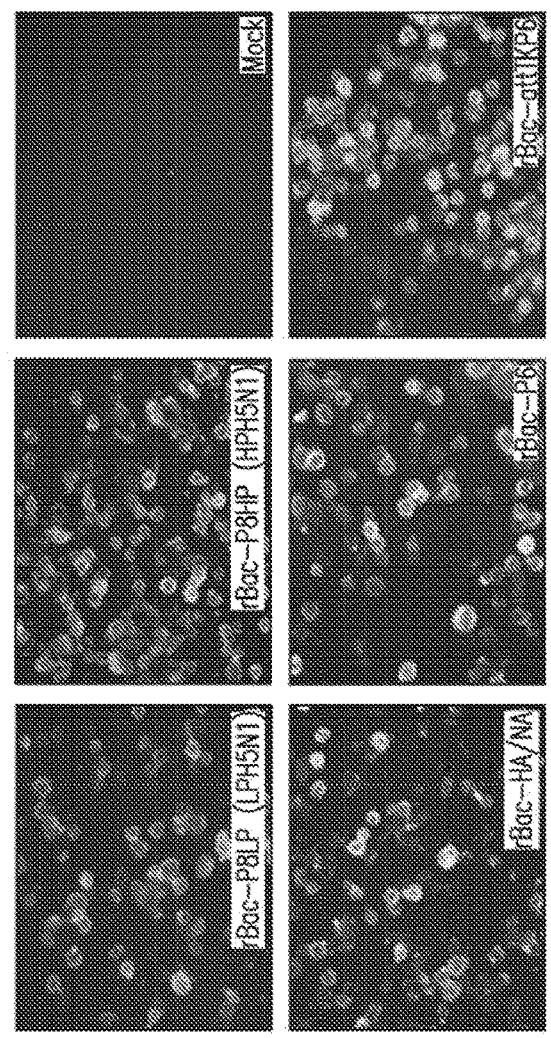
FIG. 5F. Recombinant baculoviruses stained with GP64-FITC antibody.
Figure 7:
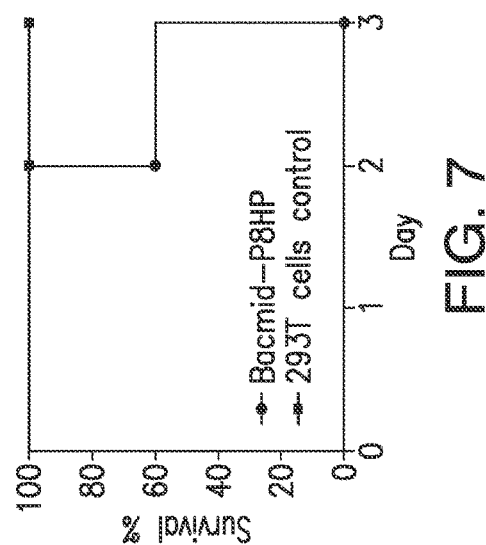
FIG. 7 provides a graph showing the survival of Bacmid-P8HP transfectant in mice.

Sequencing of recombinant plasmids and viral cDNAs was performed using SVpA-Rev primer, a combination of universal primers or custom made primers (available upon request) and the Big Dye Terminator v3.1 Cycle Sequencing kit (Applied Biosystems, Foster City, Calif.) on a 3500 Genetic Analyzer (Applied Biosystems, Foster City, Calif.) according to the manufacturer's instructions. Sequence analysis was performed using software available through the Lasergene package (DNAstar Inc., Madison, Wis.). The results are shown in FIG. 5.

Example 6

Identification of Gene Cassettes by Immunological Assays

The recombinant plasmids and recombinant baculoviruses were further checked with specific antibodies to PB2, PB2, PA, NP, NS, and HA by Immunological Fluorescent (IF) assay or Western blotting analysis. The antibodies were including Baculovirus gp64 (AcV1) antibody—Fluorescein Isothiocyanate (FITC) (Santa Cruz biotechnology Inc, Santa Cruz, Calif.), the purified chicken yolk IgY against PR8 (data not shown), monoclonal antibody (mAb) DPJY01 against H5N1 viruses, mAb Influenza A NP (9G8) (Santa Cruz), rabbit anti-Influenza A pb1 (vC-19) (Santa Cruz), mice anti-PB2 antibody (Santa Cruz), NS1 mAb (Santa Cruz), rabbit PA antibody (Santa Cruz), mAb C102 against Hemagglutinin (Santa Cruz). The second antibodies were selected by the above antibodies made by different hosts and different immunological methods, including goat anti-rabbit IgG (H+L)-FITC (Southernwest Biotech Associates Inc, Birmingham, Ala.), goat anti-mouse IgG (H+L)-FITC (Southernwest Biotech), goat anti-mouse IgG (H+L)-Rhodamine (Invitrogen, Carlsbad, Calif.), or goat anti-chicken IgG (H+L)-FITC (Southernwest Biotech). The procedures were just followed by standard methods described in the previous studies. The results were shown in FIG. 5.

Example 7

Flu Virus Rescue (A) Flu Virus Rescue In Vitro

Figure 6:
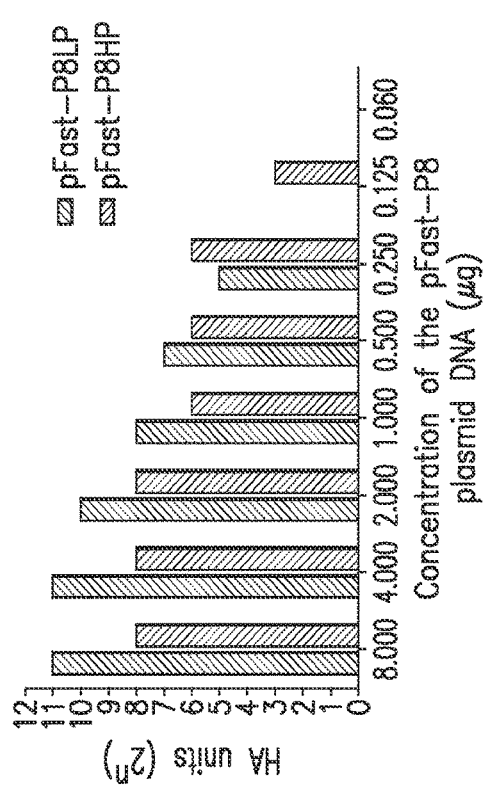
FIG. 6 provides a schematic representation of pΔFast-P8 plasmid compared with 6 plus 2 plasmids reverse genetics system.
Figure 6:
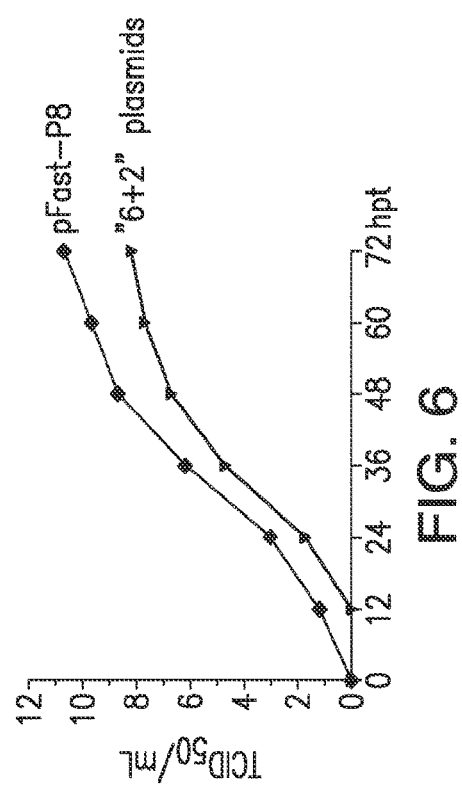

Co-cultured 293T/MDCK cells at a ratio of 100:1 ($5\times10^5$ cells per well) was seeded into each well of a 6-well tissue culture plate. The plates were incubated at 37° C. overnight. The following day, co-infection of rBacP6 with rBacH1N1$_{PR8}$, rBacP8LP or rBacP8HP recombinant baculoviruses into 293T/MDCK at different MOIs, separately. After 2 h, the cells were washed with 0.01M PBS solution, and the media were changed by Opti-MEM medium. L-(tosylamido-2-phenyl) ethyl chloromethyl ketone (TPCK)-treated trypsin (1 μg/ml) was added to the cell supernatants, and the cells were maintained till 96 hpi. Cell suspensions were seeded into 6-well tissue culture plates and incubated at 37° C. overnight before transfection. Transfections and post-transfection steps proceeded as described for the 293T/MDCK co-cultured cells incubated with 1 μg/ml of TPCK-trypsin. Supernatant of co-infected cells were collected at the times indicated in Table 3 and blind passage in either or both MDCK cells or 10-day old embryonated chicken eggs to monitor for the presence of rescued viruses. TCID$_{50}$ titers were determined in MDCK cells by the Reed and Muench method as described. Virus stocks were prepared and frozen at −80° C. until use. The results were shown in Table 4. And also, we transfected the pΔFast-P8LP and pΔFast-P8HP plasmids for control. Compared with the 6 plus 2 plasmids reverse genetics system (PR8 as a backbone), the efficiency of the one-plasmid system is much higher (FIG. 6, Table.3).

TABLE 3

Comparison of DNA amounts resulting in virus rescue.

| DNA amount (ng) | 8 plasmids/each | pΔFast-P8LP | Bacmid-P8LP |
|---|---|---|---|
| 1000 | + | + | + |
| 500 | + | + | + |
| 250 | + | + | + |
| 125 | + | + | − |
| 62.5 | + | + | − |
| 31.25 | − | + | − |
| 15.625 | − | − | − |
| 7.8125 | − | − | − |
| 3.90625 | − | − | − |
| 1.803125 | − | − | − |
| The mean DNA copies per transfected cell | ≥$8 \times 10^4$ | ≥$1 \times 10^3$ | ≥$3 \times 10^3$ |

Based on the pΔFast-H1N1$_{PR8}$ containing the HA and NA gene cassettes and the pΔFast-P6 plasmid containing all the six internal segments of PR8 virus, we prepared two recombinant Baculoviruses in Sf9 cells. After ultracentrifugation, the titers of rBac-P6 and rBac-H1N1$_{PR8}$ were around $10^7$ to $10^8$ ifu/mL. Then mixed the two viruses with or the absence of TransITL reagent (2 μL/m.o.i) and made co-infection in 293T cells. We found that PR8 virus could be rescued over an infection dose of 5 m.o.i helped with TransITL reagent. And in the absence of TransITL reagent, the virus could be rescued only at a dose of 10 m.o.i. The transfection reagent could enhance the transduction of baculovirus into nuclei. However, the efficiency was very low, which need to be passaged in embryonated eggs. The results were shown in Table.4. It indicated that influenza virus could be rescued by this Binary Baculovirus system (BBS).

To enhance the transduction efficiency, we prepared the rBac-P8LP and rBac-P8HP baculoviruses to infect 293T cells for virus rescue. In the absence of TransITL reagent, we found the reassortant of H5N1:PR8 only could be rescued even at a dose of 0.5 m.o.i. At 72 h~96 h after transfection or infection in 293T/MDCK cells, significant cytopathogenic effect (CPE) revealed and it did not need to be blind passaged into Eggs. It showed that the system showed a much higher efficient than the binary baculovirus system. The results were shown in Table.4 and Table.5. It indicated that influenza virus could be rescued by this Unary Baculovirus system (UBS).

TABLE 4

Virus rescue in 293T cells with recombinant Baculoviruses

| | | | Virus amount (m.o.i/each) | | | | |
|---|---|---|---|---|---|---|---|
| No | Viruses | Description | 10 | 5 | 1 | 0.5 | 0.1 |
| 1 | rBac-P6+ rBac-HANA (PR8) § | Co-infection | $0.50 \times 10^2$ (M); $1.58 \times 10^6$ (E) | 0 | 0 | 0 | 0 |
| 2 | rBac-P6+ rBac-HANA (PR8) * | Mixed with TransITL (2 μL/m.o.i) | $1.58 \times 10^6$ (M) | $1.58 \times 10^5$ (M) | 0 | 0 | 0 |
| 3 | rBac-P8LP † | Infection | $1.58 \times 10^5$ | $1.58 \times 10^5$ | $1.58 \times 10^4$ | 0 | 0 |
| 4 | rBac-P8LP # | Mixed with TransITL (2 μL/m.o.i) | $1.58 \times 10^5$ | $1.58 \times 10^5$ | $1.58 \times 10^5$ | $1.58 \times 10^4$ | 0 |
| 5 | rBac-P8HP ‡ | Infection | Not Do | Not Do | $1.08 \times 10^5$ | $1.08 \times 10^5$ | 0 |

The recombinant baculoviruses rBac-P6 and rBac-HANA (PR8), diluted into OptiMEM medium without serum, were co-infected into 293T/MDCK cells grown in 12 well-plate at a dose of 1, 5 or 10 m.o.i per virus, separately. At 12 hpt, an equal volume of the OptiMEM medium with TPCK-Trypsin (2 μg/mL) was added into the mixture. At 96 hpt, the virus titers of the supernatants were checked by HA and TICD$_{50}$. However, all the wells in this group were negative. The supernatants were blindly passaged into MDCK monolayer (M) or embryonated eggs (E). At 60 hpt, although the HA titer was still negative to the supernatants of the infected-MDCK cells, the virus titer in the group with the co-infected baculoviruses at a dose of 10 m.o.i per virus was $0.50\times10^2$ TICD$_{50}$/mL. And also, at 60 hpt, the virus titer in the allantoic fluids of the passaged eggs was $1.58\times10^6$ TICD$_{50}$/mL. However, all were negative in the groups with the co-infected baculoviruses at the dose of 5 m.o.i or 1 m.o.i per virus. The viruses were double-checked by HI assay with the purified chicken IgY against PR8 virus.

The recombinant baculoviruses rBac-P6 and rBac-HANA (PR8), diluted into OptiMEM medium without serum, were mixed with the TransITL reagent (2 μL/moi). Put the mixture for 45 min at room temperature and then transfected into 293T/MDCK cells grown in 12 well-plate at a dose of 1, 5 or 10 m.o.i per virus, separately. The protocol was followed by the manual of this transfection reagent. At 12 hpt, the supernatants were discarded and the cells were added with the OptiMEM medium with TPCK-Trypsin (1 µg/mL). At 96 hpt, the virus titers of the supernatants were checked by HA and TICD$_{50}$. However, all the wells in this group were negative. The supernatants were blindly passaged into MDCK monolayer. At 60 hpt, the significant CPE appeared and the virus titer was $1.58 \times 10^6$ TICD$_{50}$/mL in the group of 10 moi per virus or $1.58 \times 10^5$ TICD$_{50}$/mL in the group of 5 moi per virus. However, all were negative in the group at the dose of 1 m.o.i per virus. The viruses were double-checked by HI assay with the purified chicken IgY against PR8 virus.

The recombinant baculovirus rBac-P8LP contained the surface HA and NA gene segments of VietNam/1203/04 (H5N1) virus and all the six internal gene segments of PR8 virus. The rBac-P8LP virus was diluted into OptiMEM medium without serum and was co-infected into 293T/MDCK cells grown in 12 well-plate at a dose of 0.1, 0.5, 1, 5 or 10 m.o.i per virus, separately. At 12 hpt, an equal volume of the OptiMEM medium with TPCK-Trypsin (2 μg/mL) was added into the mixture. At 96 hpt, the significant CPE in the groups of the rBac-P8LP virus with 5 and 10 m.o.i and the virus titers of the supernatants were 1.58×105 TICD50/mL. And, the group with 1 m.o.i virus, the titer of the supernatant was 1.58×104 TICD50/mL. However, both were negative in the two groups with the virus at a dose of 0.5 m.o.i or 0.1 m.o.i. The viruses were double-checked by HI assay with the monoclonal antibody DPJY01 against H5N1 virus.

The rBac-P8LP virus was diluted into OptiMEM medium and mixed with the TransITL reagent (2 μL/moi). Put the mixture for 45 min at room temperature and then transfected into 293T/MDCK cells grown in 12 well-plate at a dose of 0.1, 0.5, 1, 5 or 10 m.o.i per virus, separately. The protocol was followed by the manual of this transfection reagent. At 12 hpt, the supernatants were discarded and the cells were added with the OptiMEM medium with TPCK-Trypsin (1 μg/mL). At 96 hpt, the virus titers of the supernatants were checked by HA and TICD50. The significant CPEs appeared in the groups of the rBac-P8LP virus with a dose of 10 m.o.i, 5 m.o.i or 1 m.o.i with a same virus titer of 1.58×105 TICD50/mL. And, the group with 0.5 m.o.i virus, the titer of the supernatant was 1.58×104 TICD50/mL. However, it was negative in the group with the virus at a dose of 0.1 m.o.i with or without blind passages.

The recombinant baculovirus rBac-P8HP contained the surface HA and NA gene segments of VietNam/1203/04 (H5N1) virus and all the six internal gene segments of PR8 virus. The rBac-P8HP virus was diluted into OptiMEM medium without serum and was co-infected into 293T/MDCK cells grown in 12 well-plate at a dose of 0.1, 0.5 or 1 m.o.i per virus, separately. At 12 hpt, an equal volume of the OptiMEM medium with TPCK-Trypsin (1 μg/mL) was added into the mixture. At 72 hpt, the significant CPE in the groups of the rBac-P8HP virus with 1 m.o.i and 0.5 m.o.i and the virus titers of the supernatants were 1.08×105 TICD50/mL. However, it was negative in the group with the virus at a dose of 0.1 m.o.i. As described above. The viruses were double-checked by HI assay with the monoclonal antibody DPJY01 against H5N1 virus.

TABLE 5

Comparison of rBac-P8LP Baculovirus rescue in A549 cells and 293T/MCK cells

| | Virus amount of rBac-P8LP (m.o.i/each) | |
|---|---|---|
| Group | 10 | 1 |
| A549 Cells † | $1.58\times10^4$ | $1.58\times10^3$ |
| 293T/MDCK co-culture # | $1.58\times10^5$ | $1.58\times10^4$ |

The recombinant baculovirus rBac-P8LP contained the surface HA and NA gene segments of VietNam/1203/04 (H5N1) virus and all the six internal gene segments of PR8 virus. The rBac-P8LP virus was diluted into OptiMEM medium without serum and was co-infected into A549 cells grown in 12 well-plate at a dose of 1, or 10 m.o.i, separately. At 12 hpt, an equal volume of the OptiMEM medium with TPCK-Trypsin (0.5 μg/mL) was added into the mixture of A549 cells. At 72 hpt, the significant CPE could be seen in the A549 group with a dose of 1 and 10 m.o.i virus and the virus titer of the supernatants was $1.58\times10^3$ $TICD_{50}$/mL (1 m.o.i) or $1.58\times10^4$ $TICD_{50}$/mL (10 m.o.i). The viruses were double-checked by HI assay with the monoclonal antibody DPJY01 against H5N1 virus.

The rBac-P8LP virus was diluted into OptiMEM medium without serum and was co-infected into 293T/MDCK cells grown in 12 well-plate at a dose of 1 or 10 m.o.i, separately. At 12 hpt, an equal volume of the OptiMEM medium with TPCK-Trypsin (2 μg/mL) was added into the mixture of 293T/MDCK cells. At 72 hpt, the significant CPE could be seen and the virus titer of the supernatants was $1.58\times10^4$ $TICD_{50}$/mL (1 m.o.i) or $1.58\times10^5$ $TICD_{50}$/mL (10 m.o.i). The viruses were double-checked by HI assay with the monoclonal antibody DPJY01 against H5N1 virus.

(B) Flu Virus Rescue In Vivo

The Bacmid-P8HP was transfected into 293T cells. After 24 h before changing the medium, the cells were collected and challenged into mice. The results shown in FIG. 7 demonstrate that Bacmid-P8HP transfectants could kill mice in 3 days.

Example 8

Additional Candidates

According to the strategies shown above, we also constructed Bacmids with the genomes from wildtype VN1203 (H5N1) virus, H9N2 (WF10att) virus, and H3N2 (Ty04att) virus. The plasmids and Bacmids are shown in Table.6.

TABLE 6

List of the constructed flu genomes

| Name | Description |
|---|---|
| Bacmid-P8LPE | ΔH5N1: 6PR8 and EGFP bi-expression box in Bacmid DNA |
| pΔFast-P8LPE | ΔH5N1: 6PR8 and EGFP bi-expression box in pΔFast-Bac1 |
| Bacmid-P8V | H5N1 (VN1203) segments in Bacmid DNA |
| pΔFast-P8V | H5N1 (VN1203) segments in pΔFast-Bac1 |
| Bacmid-P8W | H9N2 (WF10att) segments in Bacmid DNA |
| pΔFast-P8W | H9N2 (WF10att) segments in pΔFast-Bac1 |
| Bacmid-P8T | H3N2 (Ty04att) segments in Bacmid DNA |
| pΔFast-P8T | H3N2 (Ty04att) segments in pΔFast-Bac1 |

Example 9

Plasmids and Bacmids

Reverse genetic (RG) expression elements have been previously described for the generation of influenza mRNA and viral-like RNAs from the pDP2002 vector, a derivative of pHW2000 (Hoffman et al. PNAS USA 97:6108-6113 (2000), Perez et al. J Virol 77:3148-3156 (2003)). The RG 8-plasmid system for A/Puerto Rico/8/34/Mount Sinai (H1N1) (PR8) based on the pDZ vector was a kind gift from Peter Palese, Mount Sinai School of Medicine, New York, N.Y. (Schickli et al. Philos Trans R Soc Lond B Biol Sci 356:1965-1973 (2001)). The pDZ-based PR8 gene segments were sub-cloned into the pDP2002 vector in order to maintain consistency with other RG clones described below. The pDP2002-based RG 8-plasmid system for temperature sensitive A/turkey/Ohio/313053/2004 (H3N2) (Ty/04ts) and surface gene segments from A/Vietnam/1203/2004 (H5N1) with a HA gene without the polybasic cleavage site (∂H5N1) have been previously described (Pena et al. J Virol 85:456-469; Song et al. J Virol 81:9238-9248).

The plasmid pFastBac1 (Life Technologies, Grand Island, N.Y.) was modified to delete the polyhedrin promoter (plh) to generate the cloning vector p∂FB1. The RG-competent internal gene cassettes from the PR8 strain were sequentially subcloned from the pDP2002 vector into p∂FB1 using appropriate restriction sites to produce p∂FP6PR8 (~21.9 kb). The p∂FP6PR8 was further modified with the insertion of the thymidine kinase (tk) gene flanked by lambda phage attR recombination elements (attTK) with a size of 2247 bp, produced from an overlapped PCR reaction from the Baculo-Direct vector (Life Technologies). The resulting plasmid was designated p∂FP6attTKPR8. A similar strategy was used to generate a shuttle vector carrying the internal gene cassettes from Ty/04ts and the attTK element in order to generate p∂FP6attTKTy04ts. For cloning, the Quick ligation kit (New England Biolabs, Ipswich, Mass.) or DNA ligation kit for long fragments (Takara Bio Inc, Japan) were used along with either One Shot TOP10 chemically competent E. coli cells (Life Technologies) or One shot ccdB Survival™ 2 T1R competent E. coli cells (Life Technologies). At each cloning step, plasmids were verified by sequencing and gene functionality by reverse genetics or minireplicon assays (data not shown). Sequencing of recombinant plasmids was performed using a combination of universal primers (Hoffman et al. Archives of Virology 146:2275-2289 (2001)), custom primers, and the Big Dye Terminator v3.1 Cycle sequencing kit (Applied Biosystems, Foster City, Calif.) on a 3500 Genetic Analyzer (Applied Biosystems) according to the manufacturer's instructions. Sequence analysis was performed using software available through the Lasergene package (DNAstar Inc, Madison, Wis.). For minireplicon assays, plasmids pcDNA774PB1, pcDNA762PB2, pcDNA787PA and pcDNA693NP (Perez et al. Virology 249: 52-61) were used depending on the gene to be tested in the p∂FB1 vector. The pHW72-EGFP plasmid encoding the influenza EGFP reporter replicon was a gift from Robert Webster, St Jude Children's Research Hospital, Memphis, Tenn. (Hoffman et al. Virology 267: 310-317).

The plasmid pENTR-1A dual vector was used to generate multiple plasmids carrying the RG-competent surface (HA and NA) gene cassettes (Table 7 and FIG. 8). In addition, one of these constructs was further modified to carry an enhanced green fluorescent protein (EGFP) gene cassette under the control of a cytomegalovirus promoter (CMV). The following plasmids were constructed: pE64P (H1N1PR8), pE46VL (∂H5N1VN1203), and pE4E6VL (∂H5N1VN1203/EGFP). Plasmids were verified by sequencing and gene functionality by reverse genetics as described above prior to further genetic manipulation.

The Gateway LR cloning method (Life Technologies) was used to transfer the gene cassettes cloned in the pENTR-1A vector into the p∂FP6attTKPR8 and p∂FP6attTKTy04ts vectors in order to generate plasmids with a full set of reverse genetics competent influenza gene segments (Table 7 and FIG. 8). Subsequently, recombinant bacmids were produced using the MAX Efficiency DH10Bac Competent E. coli cells (Life Technologies) following the manufacturer's directions. Bacmids encoding a full set of influenza RG competent units (bcmd-RGFlu) are more stable than plasmids encoding similar genetic information (not shown). Transposition of the above recombinant shuttle plasmids was selected on 1.2% LB-Agar plates containing Bluo-gal (Sigma-Aldrich, St. Louis, Mo.), Isopropylthio-β-galactoside (IPTG) (Sigma), Gentamicin (Sigma), Kanamycin (Sigma), Tetracycline hydrochloride (Sigma) according to the instructions for the Bac-to-Bac expression system (Life Technologies). After three rounds of negative selection with antibiotics, colorless colonies were picked and bacmid DNAs were extracted and identified by PCR reactions using appropriate primer sets (sequences available upon request). The positive recombinant bacmids were designated as bcmd-P6FR8, bcmd-P8FR8 (H1N1PR8), bcmd-P8LPE (∂H5N1VN1203), bcmd-P8LPE (∂H5N1VN1203/EGFP), and bcmd-P8Ty04ts (H1N1PR8).

TABLE 7

Recombinant bcmd-RGFlu DNAs generated in this study

| Internal Gene Backbone | Acronym | Subtype | Donor vector | Entry plasmids | Eight-in-one plasmid (segment order) | Six-in-one bacmid |
|---|---|---|---|---|---|---|
| A/Puerto Rico/8/1934(H1N1) | PR8 | H1N1 | p∂FP6PR8 | N/A | N/A | bcmd-P6PR8 |
| A/Turkey/Ohio/31305304 (H3N2)ts | Ty04ts | H3N2 | p∂FP6Ty04ts | N/A | N/A | bcmd-P6Ty04ts |

| Surface Gene Segments | | | | | | Eight-in-one-bacmid |
|---|---|---|---|---|---|---|
| A/Puerto Rico/8/1934(H1N1) | PR8 | H1N1 | p∂FP6attTK$_{FP8}$ | pE64P | p∂FP8P (12$\underline{643}$578) | bcmd-P8PR8 (H1N1$_{PR8}$) |
| A/Vietnam/1203/2004 (H5N1) mod. | VN1203 | ∂H5N1 | p∂FP6attTK$_{FP8}$ | pE46VL | p∂FP8LP (12$\underline{643}$578) | bcmd-P8LP (∂H5N1$_{VN1203}$) |
| A/Vietnam/1203/2004 (H5N1) mod. | VN1203 | ∂H5N1 | p∂FP6attTK$_{FP8}$ | pE4E6VL | p∂FP8LPE (12$\underline{6E43}$578) | bcmd-P8LPE (∂H5N1$_{VN1203/EGFP}$) |
| A/Puerto Rico/8/1934(H1N1) | PR8 | H1N1 | p∂FP6attTK$_{TY04ts}$ | pE64P | p∂FP8T11 (35$\underline{642}$817) | bcmd-P8Ty04ts (H1N1$_{PR8}$) |

Figure 8D:
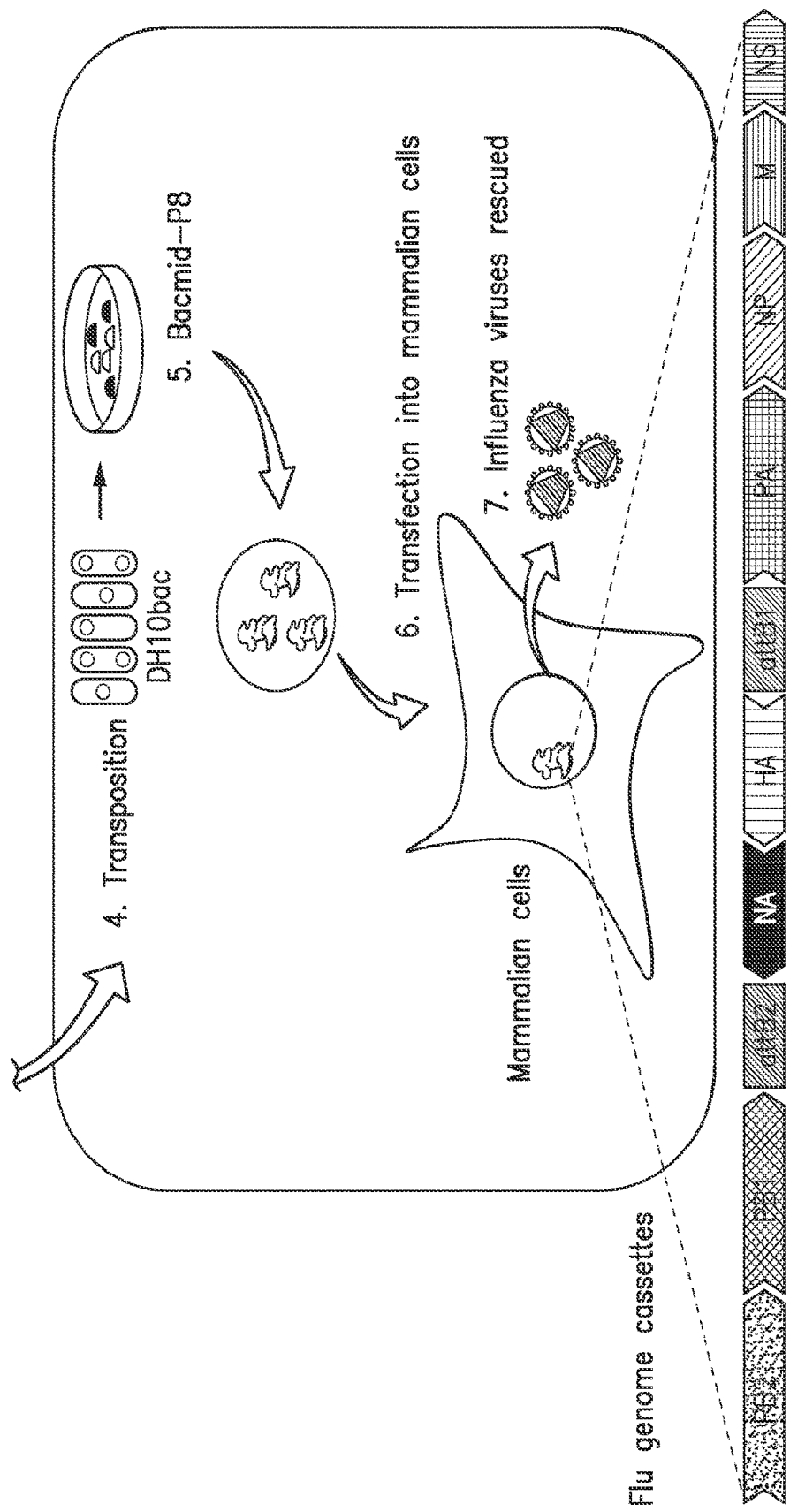
FIG. 8D shows transfection of bcmd-RGFlu into appropriate cells leads to de novo influenza virus synthesis.

FIG. 8 demonstrates a prototypical strategy for construction of a Bcmd-RGFlu vector starting with the cloning of RG competent units (bi-directional RNA pol 1 and 2 promoters flanking a cDNA copy) of the internal gene segments of a given influenza virus strain and further modification with the incorporation of lambda phage attR recombination units flanking the thymidine kinase gene, p∂FP6attTK (FIG. 8A). On a separate set of reactions, RG competent units for the HA and NA gene segments are cloned into the pENTER-1A vector to generate the pE46 vector (FIG. 8B). Using Gateway LR recombination and the plasmids p∂FP6attTK and pE46, the plasmid p∂FP8 is obtained containing 8 RG influenza virus competent units (FIG. 8C). The p∂FP8 vector contains Tn7 recombination signals, flanking the RG influenza virus clone, that are used for the transposition of the RG units into a bacmid in DH10bac E. coli cells. The resulting bcmd-RGFlu is approximately 170 kbs long. Transfection of bcmd-RGFlu into appropriate cells leads to de novo influenza virus synthesis (FIG. 8D).

FIG. 9 provides a schematic representation of de novo influenza virus synthesis from bcmd-RGFlu constructs. FIG. 9A shows PCR amplicons produced using bcmd-P8PR8F (H1N1PR8) as template with the following primer sets: Ba-PB2-1F/Ba-PB2-2341R (1), Bm-PB1-1/Bm-PB1-2341R (2), Bm-PA-1/Bm-PA-2233R (3), Bm-HA-1F/Bm-NS-890R (4), Bm-NP-1F/Bm-NP-1565R (5), Ba-NA-1F/Ba-NA-1413R (6), Bm-M-1F/Bm-M-1024R (7), and Bm-NS-1F/Bm-NS-890R (8). FIG. 9B shows PCR amplicons similar to A) except that bcmd-P8PR8 (∂H5N1VN1203) was used as the template with the following primer sets: PB2-1643F/Ba-PB-2341R (1), PB1-1240F/Bm-PB1-2341R (2), PA-892F/Bm-PA-2233R (3), H5-clvF/Bm-NS-890R (4), NP-1116F/Bm-NP-1565R (5), NA-788F/Ba-NA-1403R (6), M-741F/Bm-M-1042R (7), NS-474F/Bm-NS-890R (8). FIG. 9C shows the results of 5 µg of bcmd-P8PR8 (H1N1PR8) or bcmd-P8LP (∂H5N1) (or 8 µg of the corresponding plasmid RG set) transfected into co-cultured 293T/MDCK cells. Virus in supernatants of transfected cells were collected every 24 h until 96 hpt and titered by TCID50 in MDCK cells. FIG. 9D shows the results of 5 µg of bcmd-P8PR8 (H1N1PR8) or bcmd-P8LP (∂H5N1) (or 8 µg of the corresponding plasmid RG set) transfected into Vero cells. FIG. 9B shows the results of 5 µg of bcmd-P8LPE (∂H5N1VN1203/EGFP) transected in the indicated cells and analysed for EGFP expression and examined under an Axiophot Photomicroscope produced by Carl Zeiss (λEx of 488/543 nm, λEm of 522/590 nm for 100 ms). Pictures are representative of transection efficiency at 48 hpt (20×). Amount of ∂H5N1 virus produced at 72 hpt is indicated in Table 8. FIG. 9F provides immunofluorescence assay for HA expression from bcmd-P8LPE (∂H5N1VN1203/EGFP) transfected into 293T cells using monoclonal antibody DPJY01 against the H5 HA and fluorescein isothiocyanate (FITC)-conjugated goat anti-mice Ig (H+L) (Southernwest Biotech Associates Inc, Birmingham, Ala.). Nuclei stained with DAPI stain. Magnification is ×20. FIG. 9G provides Western-blot analysis of 293T cells transfected with either bcmd-P8LPE (∂H5N1VN1203/EGFP), bcmd-P6PR8, or mock (293T). Antibodies specific for viral PB2, PB1, PA, NP, and NS1 proteins as well as antibodies against EGFP and the host glyceraldehyde-3-phosphate dehydrogenase (GADPH) were used according to details in the materials and methods section.

Immunological Assays

Recombinant bcmd-RGFlu DNAs were checked for influenza virus protein expression using specific antibodies by either immunofluorescence assay (IFA) or western blot analysis. Antibodies used were an IgA-type monoclonal antibody (mAb) DPJY01 against HAS of H5N1 viruses prepared in house (diluted 1:500), rabbit anti-NP antibody (Novus Biologicals LLC, Littleton, Colo., diluted 1:1500), goat anti-PB1 VK-20 N-ter) (Santa Cruz Biotechnology Inc, Dallas, Tex., diluted 1:150), goat anti-PB2 VN-19 (N ter) (Santa Cruz, diluted 1:200), mouse anti-NS1-23-1 (N-ter) (Santa Cruz, diluted 1:250), rabbit anti-PA (C-ter) (Gentex Inc, Irvine, Calif., diluted 1:2000), mouse anti-HA (eEnzyme LLC, Gaithersburg, Md., diluted 1:2000), and rabbit anti-EGFP antisera (Life Technologies, diluted 1:1500). Secondary antibodies were selected accordingly, including goat anti-moase Ig (H+L)-Fluorescein isothiocyanate (FITC) (Southern Biotech, Birmingham, Ala., diluted 1:2500), horseradish peroxidase (HRP)-conjugated donkey anti-goat IgG (Santa Cruz, diluted 1:2500), HRP-conjugated goat anti-rabbit IgG (Southern Biotech, diluted 1:4000), and HRP-conjugated goat anti-mouse IgG (Southern Biotech, diluted 1:5000).

Paraffin-embedded tissues were sectioned and stained with hematoxylin, and eosin (H&E). For immunohistochemistry (IHC), the tissue sections were stained with horseradish peroxidase-conjugated rabbit anti-H1N1 NP polyclonal antibody (Bioss Inc, Woburn, Mass.). To block nonspecific antibody binding activity, the sections were blocked with 10% goat serum for 30 min (Sigma), and endogenous peroxidase activity was quenched with 1% $H_2O_2$. Finally, the staining was performed using avidin-streptavidin-peroxidase and diaminobenzidine as the substrate as described (Nishimura et al. J Gen Virol. 81:2503-2510 (2000)).

Eukaryotic Cells

Madin-Darby Canine Kidney Epithelial Cell line MDCK (ATCC CCL-34), African green monkey kidney cells Vero (ATCC CCL-81), human lung carcinoma cells A549 (ATCCCCL-185™), and swine kidney cells PK-15 (ATCC CCL-33) were maintained in Modified Eagle's medium (MEM) (Sigma) containing 10% fetal bovine serum (FBS) (Sigma). Mouse embryonic fibroblast cell line NIH-3T3 (ATCC CRL-1658) was maintained in Dulbecco's Modified Eagle's Medium (DMEM) (Gibco, Gaithersburg, Md.) with 4.5 g/L glucose, L-glutamine, and sodium pyruvate Medium, containing 10% FBS. Human embryonic kidney cells 293T (HEK293T) were cultured in Opti-MEM I (Gibco) containing 5% FBS. Mus musculus lung adenoma cells LA-4 (ATCC CCL-196) were maintained in Kaighn's Modification of Ham's F-12 Medium (ATCC, Manassas, Va.). Abelson marine leukemia virus transformed macrophage cell line RAW264.7 (ATCC TIB-71), was maintained in DMEM medium containing 10% FBS. Normal human bronchial primary epithelial cells (CAT 502K-05a) were grown in HBEM growth medium (Cell applications Inc, San Diego, Calif.), as described previously (Wan H et al. J Virol 81:5181-5191).

Transfection of Tissue Culture Cells

Transfections of reverse genetics plasmids were performed essentially as described (Hoffman et al. PNAS USA 97:6408-6113 (2000)). Transfections with recombinant bacmid DNAs were optimized based on the parameters discussed in detail in the paragraphs below. Recombinant bacmid DNAs were extracted by PureLink HiPure plasmid maxiprep kit (Life Technologies) and then purified by the UltraClean Endotoxin Removal Kit (MO Bio Laboratories Inc, Carlsbad, Calif.). Cell suspensions were seeded into 6-well tissue culture plates and incubated at 37° C. overnight before transfection. For 293T/MDCK co-cultured cells (10:1), $1 \times 10^6$ cells were transfected with 5 µg Bacmid DNAs or 1 µg each plasmid in RG 8-plasmid set. At 12 h post-transfection (hpt), the transfection media was removed and replaced by 1 mL of OptiMEM medium supplemented with L-(tosylamido-2-phenyl) ethyl chloromethyl ketone-treated bovine trypsin (TPCK-Trypsin, 1 μg/mL, Worthington, Lakewood, N.J.) and incubated for up to 144 hpt (24). Transfections and post-transfection steps for other cells (Table 8) proceeded similarly except that different concentrations of TPCK-trypsin were used, as follows: For HBEC, LA-4, RAW264.7, 3T3-NIH, and A549 cells, $1\times10^6$ cells in 6-well plates were supplemented at 12 hpt with serum-free media containing 0.5 μg/ml of TPCK-trypsin. Vero cells were incubated with OptiMEM containing 0.5 μg/ml of TPCK-trypsin, replenished daily. PK-15 cells were supplemented with TPCK-trypsin at a concentration of 0.25 μg/mL. Tissue culture supernatants were collected at the times indicated and, where indicated, blind passaged in either 10-day old specific pathogen free (SPF) embryonated chicken eggs or MDCK cells or both to monitor for the presence of rescued viruses. Virus stocks were prepared and frozen at –80° C. until use. $TCID_{50}$ titers were determined in MDCK cells by the Reed Muench method as described (Reed et al. Am. J. Hyg. 27 493-497 (1938)). Virus titers were graphed and statistical analysis performed using the Prism 6 software (GraphPad, La Jolla, Calif.). Comparisons between two treatment means were carried out using a two-tailed paired-Student t test. Multiple comparisons were carried out by two-way analysis of variance (ANOVA). Differences were considered statistically significant at a P value of <0.05.

Transfection-Based Inoculation in Mice

Animal studies were approved by the Institutional Animal Care and Use Committee of the University of Maryland, College Park. 5 week-old DBA/2J female mice (Charles River Laboratories, Frederick, Md.) were anesthetized with isoflurane prior to intranasal inoculation. For pathogenesis studies, each mouse (n=5/group) received $5\times10^6$ 293T cells previously transfected with either 25 μg of bcmd-RGFlu DNA or 40 μg of plasmid RG DNA (5 μg of each plasmid) and TransIT-LTI at a 1:2 ratio DNA/μL transfection reagent). At 6 hpt, transfected cells were re-suspended in transfection tissue culture media, spun down at 1,000 rpm for 5 min. Subsequently, the transfection media was removed and cells re-suspended in 100 μl of OptiMEM and intranasally inoculated into mice. Negative control mice received non-transfected 293T cells ($5\times10^6$ cells in 100 μl/mouse). Positive control mice were intranasally inoculated with wild type PR8 virus ($10^4$ $TCID_{50}$/100 μl/mouse). Mice were monitored daily for 14 days post-inoculation (dpi) for clinical signs of disease including lack of grooming, presence of rough coat, respiratory distress or discharge, neurological signs, body weight loss, and survival. A scoring system was used to euthanize mice if a moribund state was reached. Alternatively mice were euthanized by 14 dpi. Euthanized or dead mice were subjected to necropsy. The left lungs and half of cerebrum were collected and stored in –80° C. for determination of the titers of rescued virus. The right lung and the other half of cerebrum were fixed in 10% formalin and subsequently embedded in paraffin for immunohistochemistry assay (IHC). For virus titration, the tissues were weighted and homogenized with a Tungsten carbide bead (200 mm) in 0.01M PBS to produce a 10% (w/v) homogenates, which were oscillated at 50×1/s for 3 min in TissueLyser LT (Qiagen). After centrifugation at 12,000 rpm for 10 min, 100 μL of the supernatants were collected and serially diluted into MDCK plates. Virus titers were subsequently measured by $TCID_{50}$ assays.

For TBI vaccination studies, mice were inoculated as explained before, except that 1×107 transfected-293T cells/ 100 μl/mouse were used. Each TBI experimental group consisted of 15 mice/group. Negative control mice (n=10) inoculated with non-transfected 293T cells were included. In addition, a vaccine control group (n=8) was included. The vaccine control group was intramuscularly vaccinated with a formalin-inactivated PR8 virus (killed virus vaccine) prepared in house using Montanide™ ISA50V2 (Seppic Inc, Fairfield, N.J.) as adjuvant. At 15 days post-priming, mice were boosted with a second dose of vaccine identical to the prime vaccine for each group. Mice were bled using the submandibular bleeding method at day –1, 7, 14, 21, 28, 35 and 42 after primary immunization to test antibody titers. For hemagglutination inhibition assays (HI), the sera were collected, aliqnoted and then diluted ¹/₁₀ with receptor-destroying enzyme (RDE-II, Denka Seiken Co, Tokyo, Japan) and incubated at 37° C. overnight to remove unspecific binding activity. Subsequently, the HI assay was performed as described (16, 26), NP antibodies were identified by blocking ELISA (Synbiotics Corporation, College Park, Md.). The ratio of the OD630 value of the sample wells (S) to that of the negative control wells (N) was calculated, and S/N values≤0.5 were considered positive (27). At day 21 post-priming, mice were intranasally challenged with 100 MLD50 of PR8 virus. After challenge, mice were monitored for clinical signs as explained above.

FIG. 10 provides the results of transfection-based inoculation of bcmd-P8PR8 leading to lethal PR8 virus replication in mice. 5 week-old DBA/2J mice were intranasally inoculated with 100 μl of inoculum containing 5×106 293T cells, which have been transfected 6 h earlier with either 25 μg of Bcmd-P8PR8 (H1N1PR8) or 40 μg of the corresponding 8-plasmid RG DNAs. Negative control mice received 5×106 non-transfected 293T cells, whereas positive control mice were intranasally inoculated with wt PR8 virus (104 TCID50/100 μl). Mice were monitored for clinical signs, including body weight changes (FIG. 10A) and survival (FIG. 10B). At the time of dead, mice were necropsied, lungs and brain collected and analyzed for levels of virus in tissues by TCID50 assay in MDCK cells (FIG. 10C). A section of the collected tissues were subjected to IHC for detection of viral antigen (NP), which is indicated by the presence of a brown precipitate as described in the materials and methods (representative staining marked with arrows FIG. 10D).

Results

Virus Generation in Tissue Culture Cells from bcmd-RGFlu DNA

Figure 9A:
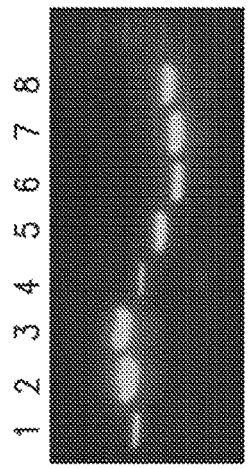
FIG. 9A shows PCR amplicons produced using bcmd-P8PR8 (H1N1$_{PR8}$) as template.
Figure 9C:
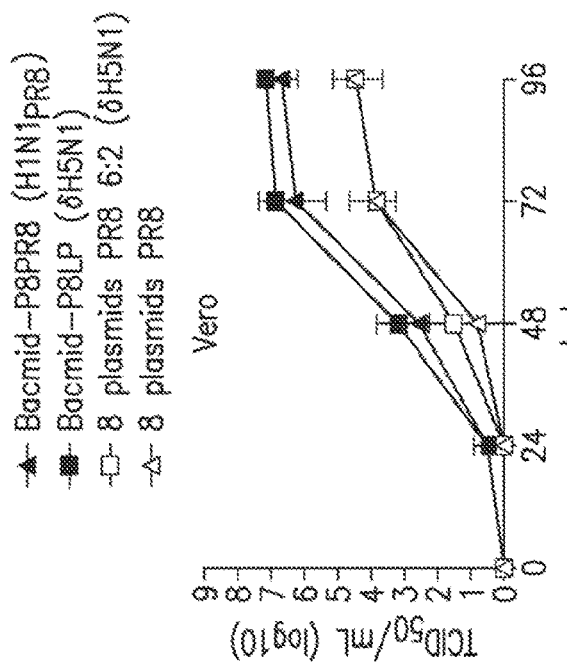
FIG. 9C shows the results of transfecting 5 µg of bcmd-P8PR8 (H1N1$_{PR8}$) or bcmd-P8LP (ƏH5N1) (or 8 µg of the corresponding plasmid RG set) into co-cultured 293T/MDCK cells.
Figure 9B:
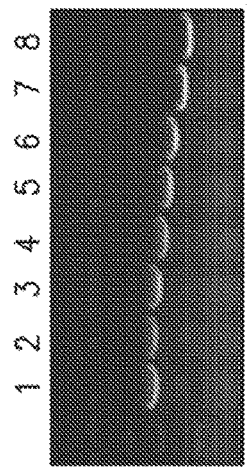
FIG. 9B shows PCR amplicons produced using bcmd-P8PR8 (ƏH5N1$_{VN1203}$).
Figure 9D:
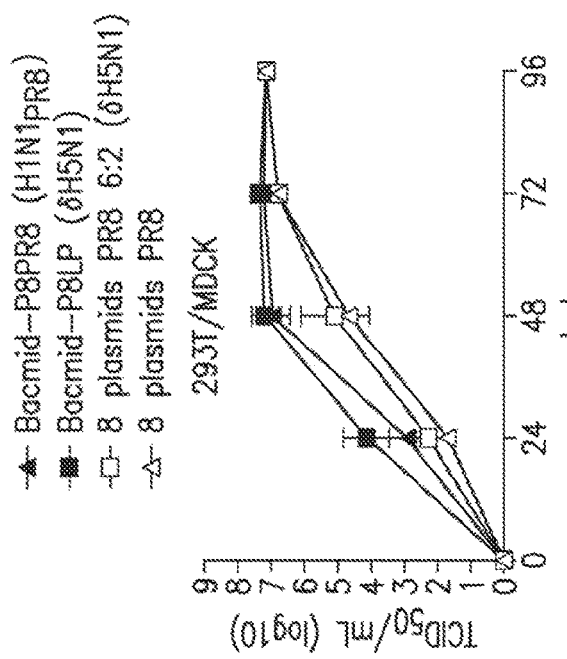
FIG. 9D shows the results of transfecting 5 µg of bcmd-P8PR8 (H1N1$_{PR8}$) or bcmd-P8LP (ƏH5N1) (or 8 µg of the corresponding plasmid RG set) into co-cultured into Vero cells.

Studies were performed to determine whether endotoxin-free bcmd-RGFlu DNAs (FIG. 8 and Table 7) were able to generate influenza de novo, and to estimate the minimum amount of DNA required for bacmid rescue compared to the 8-plasmid RG system. After insertion of the RG influenza virus clone, the bacmid vector is ~170 kb (Table 7). Initially, bcmd-P8PR8 (H1N1$_{PR8}$) was produced encoding a RG influenza virus infections clone of the PR8 virus. Subsequently, another construct was produced, bcmd-P8LP (∂H5N1$_{VN1203}$), encoding 6 RG units from the internal gene segments of PR8 and 2 surface gene segments RG units from a low pathogenic version (∂H5N1) of A/VietNam/1203/ 2004 (H5N1). PCR reactions from bcmd-P8PR8 (H1N1$_{PR8}$) and bcmd-P8LP (∂H5N1$_{VN1203}$) revealed amplicons consistent with the presence of 8 influenza gene segments (FIGS. 9A and 9B). In order to test whether other cell types were amenable for transfection and de novo influenza virus synthesis from the recombinant bcmd-RGFlu DNAs, an additional construct, the bcmd-P8LPE (∂H5N1$_{VN1203/EGFP}$), was constructed carrying EGFP under the control of a CMV RNA pol II promoter (Table 7). An optimization of transfection conditions using 293T cells was carried out to maximize influenza virus rescue efficiency. As little as 250 ng of bcmd-P8LPE (∂H5N1$_{VN1203/EGFP}$) was sufficient to rescue influenza virus compared to the 500 ng of total plasmid RG DNA (62.5 ng/each plasmid) that was required using the 8-plasmid system (not shown). If an extrapolation is made based on DNA molecule copy numbers, influenza virus rescue required $1.25 \times 10^9$ copies of bcmd-RGFlu DNA compared to $9.05 \times 10^{10}$ copies of plasmid DNA. When 20 μg of bacmid DNA was used, significant precipitation of DNA/transfection reagent was observed. Thus, for subsequent studies bacmid DNA in the range of 250 ng to 5 μg was used with a 1:2 ratio of DNA (μg) versus transfection reagent (μl). Using bcmd-P8PR8 (H1N1$_{PR8}$), influenza PR8 virus titers reached $2.32 \times 10^7$ TCID$_{50}$/ml at 48 hpt; about 150 times higher than the amount of virus obtained using the corresponding RG reverse genetics plasmids ($1.58 \times 10^5$ TCID$_{50}$/ml, FIG. 9C). In Vero cells, which are usually harder to transfect than 293T cells, PR8 virus titers from transfected bcmd-P8PR8 (H1N1$_{PR8}$, 5 μg/$10^6$ cells) were $1.58 \times 10^7$ TCID$_{50}$/ml by 72 hpt, over 300 times higher than those obtained from cells transferred with the 8-plasmid RG system ($5.00 \times 10^4$ TCID$_{50}$/ml, FIG. 9D, P<0.05). Using bcmd-P8LP (∂H5N1), the amount of influenza ∂H5N1 virus obtained was higher in 293T/MDCK ($5 \times 10^7$ TCID$_{50}$/ml, 48 hpt) and Vero ($1.58 \times 10^7$ TCID$_{50}$/ml, 72 hpt) cells compared to those obtained from the corresponding 8-plasmid RG system ($1.08 \times 10^6$ TCID$_{50}$/ml and $1.08 \times 10^4$ TCID$_{50}$/ml, respectively, P<0.05). Taken together, these results showed that transfection of a bcmd-RGFlu DNA resulted in de novo influenza synthesis with efficiencies superior to the 8-plasmid system.

Figure 9G:
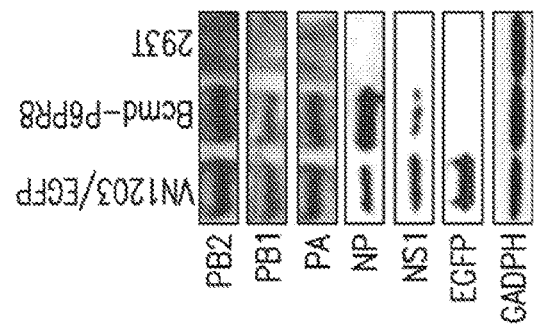
FIG. 9G provides Western-blot analysis of 293T cells transfected with either bcmd-P8LPE (ƏH5N1$_{VN1203/EGFP}$), bcmd-P6PR8, or mock (293T).
Figure 9F:
FIG. 9F provides immunofluorescence assay for HA expression from bcmd-P8LPE (ƏH5N1$_{VN1203/EGFP}$) transfected into 293T cells using monoclonal antibody DPJY01.
Figure 9E:
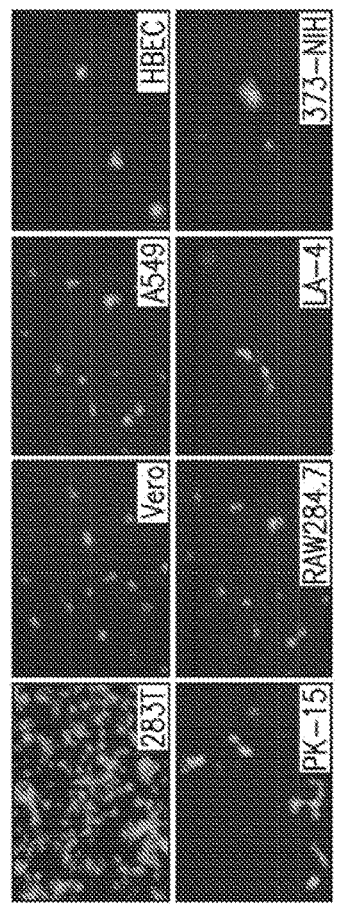
FIG. 9E shows the results of 5 µg of bcmd-P8LPE (ƏH5N1$_{VN1203/EGFP}$) transfected in the indicated cells and analyzed for EGFP expression.

When 5 μg of bcmd-P8LPE (∂H5N1$_{VN1203/EGFP}$) was used to transfect $1 \times 10^6$ 293T cells, approximately 99% of those cells showed positive GFP expression by 48 hpt (FIG. 9E). In human-origin lung carcinoma A549 cells, transfection with bcmd-P8LPE (∂H5N1$_{VN1203/EGFP}$) resulted in expression of EGFP by 48 hpt (FIGS. 9E and 9G) and lead to $1.08 \times 10^6$ TCID$_{50}$/ml of ∂H5N1 virus by 72 hpt (Table 8). In addition, human primary respiratory epithelial cells (HBEC) generated influenza virus by 72 hpt, although its detection was dependent on a blind passage in 10-day old chicken eggs ($1.08 \times 10^7$ TCID$_{50}$/ml after blind passage), consistent with their low transection efficiency (Table 8 and FIG. 9E). Likewise, transfected swine-origin PK15 cells generated detectable ∂H5N1 virus by 72 hpt after blind passage in MDCK cells ($1.08 \times 10^5$ TCID$_{50}$/ml) (Table 8 and FIG. 9E). Differences in virus rescue efficiency can be partly attributed to differences in transfection efficiency based on EGFP expression as shown in FIG. 9E. As expected, no virus was obtained with either bcmd-RGFlu or RG plasmids transfected into mouse cells (Table 8 and data not shown), consistent with the lack of activity of the hpoII in these types of cells. In contrast, EGFP expression was readily detected in mouse cells (FIG. 9E and Table 8). Additional evidence of proper expression of influenza virus proteins from bcmd-RGFlu cells in 293T cells was observed by IFA and western blot analysis (FIGS. 9F and 9G).

TABLE 8

Rescue Efficiency of bcmd-P8LPE
(∂H5N1$_{VN1203/EGFP}$) in various cell lines

| Cell line | Origin | Virus titer by 72 hpt (TCID$_{50}$/mL) |
|---|---|---|
| A549 | Human lung carcinoma | $1.0 \times 10^6$ |
| PK-15 | Swine kidney | $1.0 \times 10^5$ |
| HBEC | Human primary respiratory epithelial | $1.0 \times 10^7$ |
| LA-4 | Mouse lung adenoma | Negative |
| RAW264.7 | Mouse macrophage | Negative |
| 3T3-NIH | Mouse embryonic fibroblast | Negative |

* Bcmd-P8LPE (∂H5N1$_{VN1203/EGFP}$) was transfected into the indicated cells as described in the materials and methods. Virus titers in tissue culture supernatants from transfected cells at 72 hpt were analyzed in MDCK cells.
Blind passage of 72 hpt supernatants was needed in order to detect live virus from transfected cells.

A Transfection-Based Inoculation Method Leads to Production of Lethal PR8 Virus in Mice from bcmd-P8PR8 (H1N1$_{PR8}$).

Figure 10B:
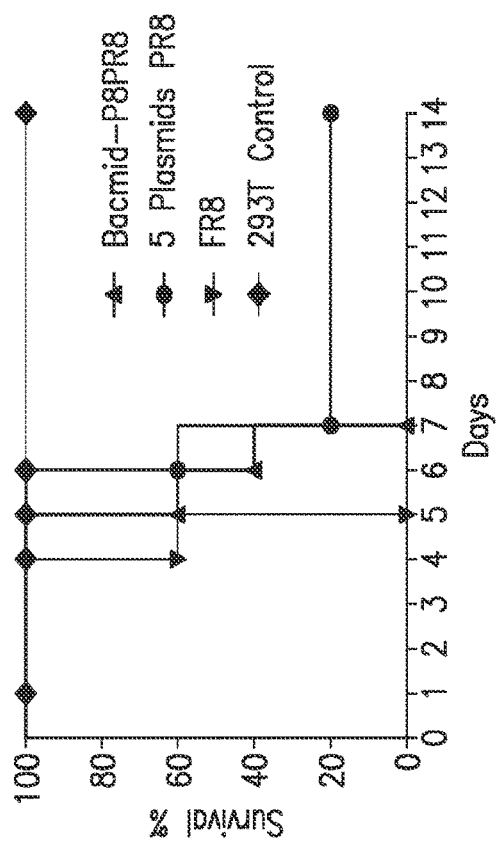
FIG. 10 provides the results of transfection-based inoculation of bcmd-P8PR8 leading to lethal PR8 virus replication in mice.
FIG. 10A provides clinical signs, including body weight changes and FIG. 10B provides survival data.
FIG. 10C provides analysis for levels of virus in tissues by TCID$_{50}$ assay in MDCK cells.
FIG. 10D provides IHC data for detection of viral antigen (NP), indicated by the presence of a brown precipitate (representative staining marked with arrows).
Figure 10A:
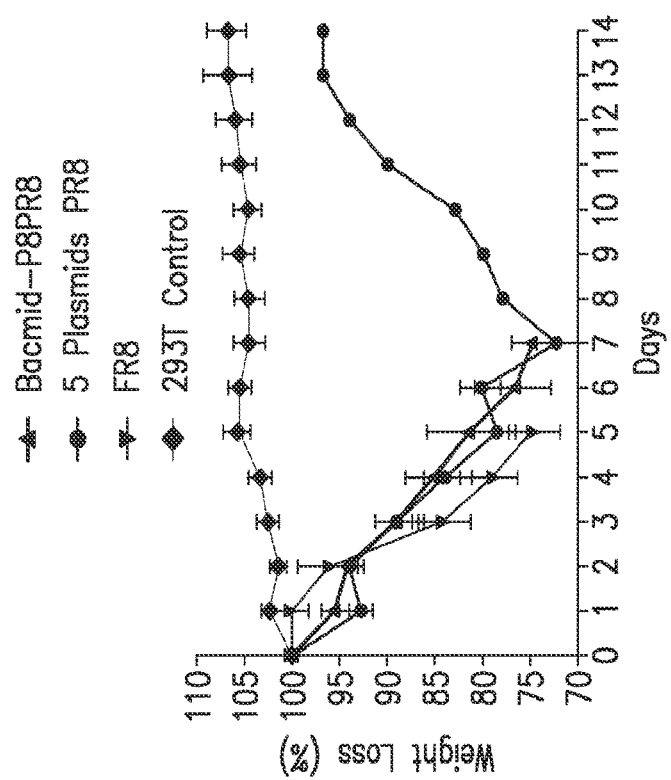
Figure 10D:
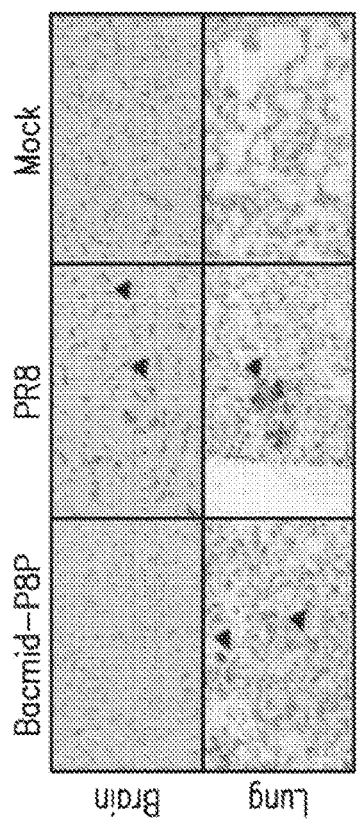
Figure 10C:
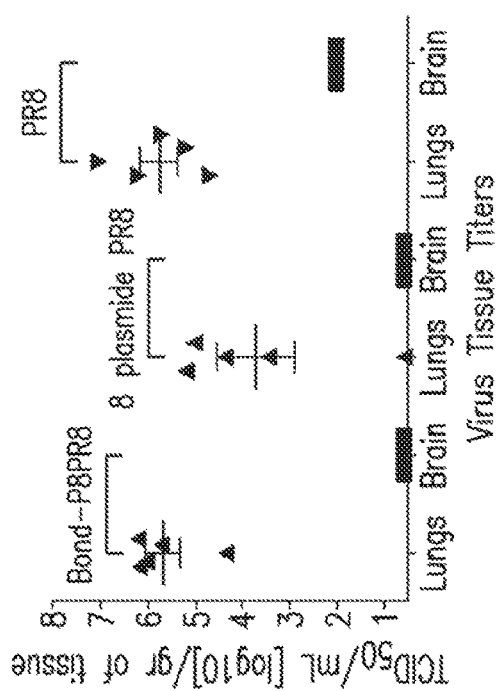

A transfection-based inoculation (TBI) method was developed in which 293T cells previously transfected with a full set of RG competent plasmids were inoculated into ferrets resulting in effective influenza virus infection in vivo (Kimbie et al. PNAS USA 108: 12084-12088 (2011)). Because the hpoII promoter is not active in mouse cells, TBI was used to demonstrate whether 293T cells, which were previously transfected with bcmd-P8PR8 (H1N1$_{PR8}$) and subsequently inoculated intransally in mice, would generate influenza virus in vivo. At 6 hpt, 293T cells were lifted from the plate, re-suspended in tissue culture media and inoculated intranasally into mice. Each mouse received 100 μl of cell suspension containing $5 \times 10^6$ cells (5 μg of bcmd-P8PR8 (H1N1$_{PR8}$)/$10^6$ cells). Alternatively, another group of mice received cells previously transfixed with the 8-plasmid PR8 RG system (8 μg total DNA/$10^6$ cells). DBA/2J mice (n=5/group) receiving 293T cells transfected with either the bcmd-P8PR8 or the 8-plasmid PR8 RG, started to show signs of disease similar to mice challenged with $10^4$ TCID$_{50}$ of the wild type PR8 virus (FIG. 10A). By 7 dpi, all mice in the bcmd-P8PR8 (H1N1$_{PR8}$) group as well as 4 out 5 mice in the 8-plasmid PR8 RG succumbed to the infection. Compared to mice challenged with wt PR8 virus, there was 24-48 h delay in the time of death in the bcmd-P8PR8 (H1N1PR8) and 8-plasmid PR8 RG groups, respectively, which are consistent with the kinetics of weight loss over time (FIG. 10B). Mice in the bcmd-P8PR8 (H1N1$_{PR8}$) group showed a tendency to succumb to the infection earlier than mice in the 8-plasmid PR8 RG group. This observation was consistent with the levels of virus detected in the lungs of mice at the time of death (FIG. 10C). One mouse in the 8-plasmid group appeared to not have been infected during the TBI procedure and show no evidence of virus replication by 14 dpi. Mice that received either the bcmd-P8PR8 (H1N1$_{PR8}$) or 8-plasmid PR8 RG showed no evidence of virus infection in the brain, unlike the mice that were challenged with the PR8 virus (FIGS. 10C and 10D). This difference was an important feature from a vaccine perspective since an in vivo RG vaccination strategy would require the virus to have replication limited to the respiratory tract.

Transfection-Based Inoculation of a bcmd-RGFlu Encoding a Temperature Sensitive H1N1 Virus Protects Mice Against Lethal Challenge.

To determine whether the TBI/bcmd-RGFlu system could protect against challenge with the virulent PR8 virus, the bcmd-P8Ty04ts (H1N1$_{PR8}$) was created encoding the temperature sensitive internal gene segments backbone from Ty04 and the surface gene segments from the PR8 strain (Table 7). Transfection of the bcmd-P8Ty04ts (H1N1$_{PR8}$) or the corresponding 8-plasmid-RG system into 293T cells was performed as described above at 33° C. (not shown), 35° C. (FIGS. 11A and 11B) and 37° C. (not shown). The Ty04ts (H1N1$_{PR8}$) virus was readily detected in 293T/MDCK and Vero cells, although, as expected, with lower efficiency than with bcmd-P8PR8 (H1N1$_{PR8}$) encoding the wild type PR8 virus. However, at 120 hpt, 293T/MDCK co-culture cells (FIG. 11A) or Vero cells (FIG. 11B) transfected with bcmd-P8Ty04ts (H1N1$_{PR8}$) produced ~100-fold more Ty04ts (H1N1$_{PR8}$) virus than those transfected with the 8-plasmid RG system (P<0.05).

Figures 11A, 11B:
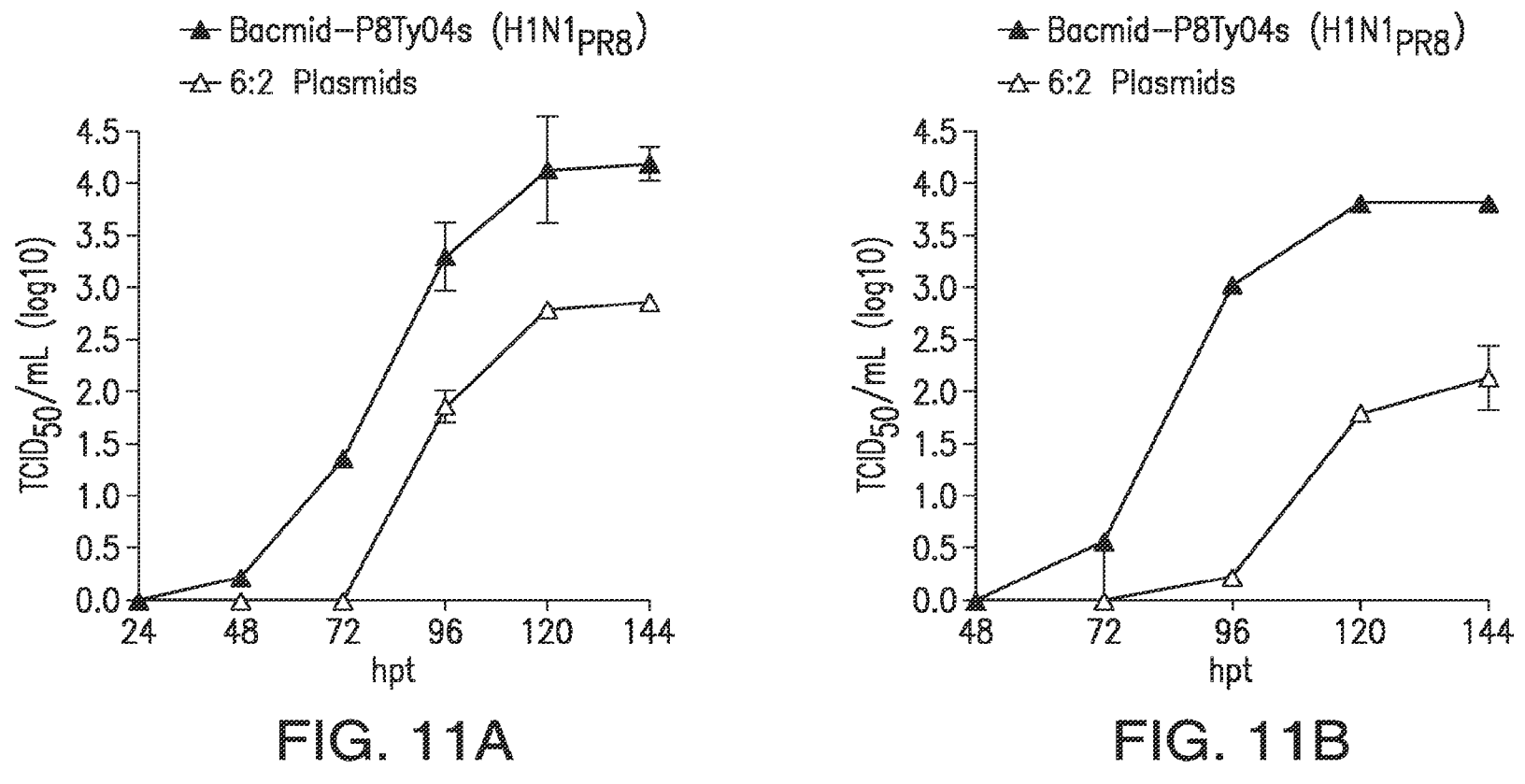

For mouse studies, negative controls included mock-transfected cells and 293T cells transfected with bcmd-P6Ty04ts, encoding the 6 internal gene segments of Ty04ts (Table 7). A prime-boost strategy, 16 days apart, was followed with mice intranasally inoculated with transfected 293T cells collected at 6 hpt (107 cells/mouse, FIG. 11C). Positive control mice received inactivated PR8 virus intramuscularly, two doses with the second dose administered 16 days post-priming. At 7 days post-boost, mice were challenged with 100 MLD50 of the PR8 virus. The study showed that TBI/bcmd-P8Ty04ts (H1N1PR8) vaccination resulted in only one dead mouse out of 15 by 14 days post-challenge, which corresponds to 93% survival (FIG. 11D). In contrast, in the corresponding TBI/8-plasmid group, 7 mice died out 15 (53% survival). In the TBI/bcmd-P6Ty04ts group, 13 mice died out 15 (13% survival), suggesting that the internal backbone of Ty04ts virus could provide limited protection against challenge. No survivors were observed in the mock-transfected 293T cell group (n=10), whereas 100% of mice survived in the KV vaccine group (n=8). Body weight loss was observed in all TBI groups indicative of active PR8 virus replication after challenge, although mice in the TBI/bcmd-P8Ty04ts (H1N1PR8) showed the least variation in body weight and no discernible clinical signs (FIG. 11E). Taken together, these results suggest that TBI vaccination with a bcmd-RGFlu resulted in protection of mice against aggressive influenza virus challenge. Lower protection in the 8-plasmid group compared to the bcmd-P8Ty04ts (H1N1PR8) was likely due to differences in virus rescue efficiency (FIGS. 11A and 11B). Except for the inactivated vaccine positive control group, no correlation between seroconversion and predictive protection could be established. Neither hemagglutination inhibition assays (Table 9) nor viral NP protein ELISA (not shown) revealed seroconversion against influenza in the TBI groups prior to challenge. These results were not completely unexpected since previous studies have shown that vaccination with live attenuated influenza vaccines can often results in serological responses below the limit of detection (Pena et al. J Virol 85:456-469 (2011)). In this particular case, virus replication of an attenuated strain generated from either a bacmid or plasmid RG set might have been even lower than by direct inoculation of the virus. Analysis of mucosal immunity may reveal a better understanding of the mechanism of protection imparted by the TBI method.

TABLE 9

HI Titers against PR8 in mice pre- and post-challenge

| Mouse # | bcmd-P8Ty04ts (H1N1$_{PR8}$) | 6:2 Plasmids | Bcmd-P6Ty04ts | KV[a] | 293T |
|---|---|---|---|---|---|
| 1 | <10/640[b] | <10/† | <10/† | 320/640 | <10/† |
| 2 | <10/640 | <10/640 | <10/† | 640/640 | <10/† |
| 3 | <10/640 | <10/320 | <10/320 | 320/320 | <10/† |
| 4 | <10/1280 | <10/† | <10/† | 640/1280 | <10/† |
| 5 | <10/320 | <10/† | <10/† | 640/1280 | <10/† |
| 6 | <10/320 | <10/† | <10/† | 640/1280 | <10/† |
| 7 | <10/640 | <10/640 | <10/† | 320/640 | <10/† |
| 8 | <10/640 | <10/† | <10/† | 320/320 | <10/† |
| 9 | <10/320 | <10/640 | <10/† | | <10/† |
| 10 | <10/† | <10/† | <10/† | | <10/† |
| 11 | <10/640 | <10/320 | <10/† | | |
| 12 | <10/640 | <10/† | <10/† | | |
| 13 | <10/1280 | <10/640 | <10/† | | |
| 14 | <10/640 | <10/320 | <10/† | | |
| 15 | <10/640 | <10/320 | <10/320 | | |

[a]KV: killed PR8 virus vaccine
[b]Pre-challenge corresponds to 21 days post-vaccination (7 days post-boost)
†Dead Aspects of the present invention, as demonstrated by the Examples above, addresses the need for alternatives to production of influenza vaccines in systems other than eggs or tissue culture cells, and provides a universal influenza vaccine that does not require annual reformulation. The present invention involves retargeting the host immune response and simulating the production of broadly reactive antibodies against the HA and/or other viral proteins.

The present example demonstrates the use of bacmids to overcome the limitations of cloning a full influenza RG set into a single DNA unit constrained by stability or copy number. Two sets of high copy number plasmids were initially constructed, one to contain a RG set of the internal gene segments of the influenza strain in question (PR8 or Ty04ts) and another to contain the RG units for the HA and NA surface genes (Table 7). Both sets of these plasmids had additional molecular features to generate recombinant bacmids in which the HA and NA RG cassettes could be easily incorporated by recombination while maintaining the chosen influenza strain backbone. Bcmd-RGFlu constructs had improved transfection efficiency (≥100 fold) compared to the 8-plasmid counterparts particularly in hard-to-transfect Vero cells (FIG. 9). This represented a significant improvement over previous reports regarding transfection of Vero cells. Fodor reported the generation of 10-20 PFU of influenza virus from 107 Vero cells by 4 dpi (Poon et al. J. Virol 73:3473-3476 (1999)). Wood and Robertson generated an H5N1 reference vaccine strain in Vero cells by reverse genetics but did not report the rescue efficiency (Wood et al. Nat Rev Microbiol 2:842-847), whereas PR8 or PR8-based viruses were generated in Vero cells with low efficiency (<103 PFU/mL). The present studies showed that virus rescue was possible also in human primary bronchial epithelial cells, although the amount of virus produced was initially below the limit of detection and needed amplification through blind passage in eggs. A similar observation was noticed using swine PK15 cells, in which the hpoll is expected to work less efficiently. These observations, demonstrate the use of bcmd-RGFlu as platform for vaccination against influenza in hosts such as humans or pigs.

Since the hpoll promoter shows no activity in mouse cells, a transfection-based inoculation system was used to determine whether the bcmd-RGFlu DNA would work in vivo. 293T cells transfected with either bacmid or plasmid DNA were inoculated into mice by 6 hpt, a time in which very few virus particles, if any, were predicted to being produced. In fact, 6 hpt supernatants were tested for the presence of virus, which was found to be below the limit of detection after two blind passages in eggs (data not shown). It is therefore believed that transfected cells remain alive in the respiratory tract of mice long enough to produce influenza virus particles capable of establishing an influenza infection (FIG. 10). This observation is also consistent with the protection seen against lethal influenza challenge in mice that received a bacmid encoding a temperature sensitive influenza virus vaccine through TBI (FIG. 11). Although the TBI vaccination strategy did not prevent against body weight loss after challenge, there was remarkable protection, with 14 out of 15 mice surviving in the group that received the bcmd-P8Ty04ts (H1N1PR8). These results were encouraging to explore alternative delivery strategies in order to induce better protection against influenza using bcmd-RGFlu DNAs. The bcmd-RGFlu DNAs described here can be easily converted into recombinant baculoviruses for an alternative method of DNA delivery into cells. Furthermore, the bcmd-RGFlu DNAs have significantly more cloning capacity than plasmids, which would allow including additional virus- or host-based strategies aimed at improving immune responses to influenza. In summary, the present invention provides a novel strategy with the potential to produce live influenza viruses de novo through in vivo reverse genetics. This strategy is not limited to influenza but amenable for other pathogens (pathogenic agents) and may overcome the current limitations of DNA vaccines.

What is claimed is:

1. A method of in vivo synthesis of a viral vaccine comprising, providing to a mammal one or more vectors comprising one or more exogenous DNA constructs, wherein the one or more exogenous DNA constructs encode the necessary components for the generation of a live influenza virus, wherein the necessary components are expressed in the mammal allowing for the generation of a live influenza virus.

2. The method of claim 1, wherein one or more copies of at least a portion of a genome of the live influenza virus are expressed in the cell.

3. The method of claim 2, wherein multiple copies of the genome are expressed in the cell.

4. The method of claim 1, wherein the vector comprises a bacmid, or a baculovirus expression system.

5. The method of claim 1, wherein the vector comprises a bacmid and a reverse genetics competent unit of influenza A virus.

6. The method of claim 1, wherein the vector comprises protein expression units and genome transcription units under the control of appropriate promoters.

7. The method of claim 1, further comprising protein expression units under the control of RNA pol II promoters and viral transcription units under the control of RNA pol I promoters.

8. The method of claim 1, wherein the live influenza virus is a live attenuated influenza vaccine.

9. The method of claim 1, wherein the vector comprises a reverse genetics competent unit comprising influenza virus.

10. The method of claim 1, wherein providing to a subject one or more vectors comprises administering a cell to the subject wherein the cell comprises the one or more vectors.

11. The method of claim 1, wherein the live influenza virus stimulates an immune response in the subject to the influenza virus.

* * * * *

```
                         SEQUENCE LISTING

<160> NUMBER OF SEQ ID NOS: 63

<210> SEQ ID NO 1
<211> LENGTH: 21
<212> TYPE: DNA
<213> ORGANISM: Artificial Sequence
<220> FEATURE:
<223> OTHER INFORMATION: synthetic construct; primer

<400> SEQUENCE: 1
attcataccg tcccaccatc g                                        21

<210> SEQ ID NO 2
<211> LENGTH: 26
<212> TYPE: DNA
<213> ORGANISM: Artificial Sequence
<220> FEATURE:
<223> OTHER INFORMATION: synthetic construct; primer

<400> SEQUENCE: 2
caggatccct attaatattc cggagt                                   26

<210> SEQ ID NO 3
<211> LENGTH: 18
<212> TYPE: DNA
<213> ORGANISM: Artificial Sequence
<220> FEATURE:
<223> OTHER INFORMATION: synthetic construct; primer

<400> SEQUENCE: 3
actccggaat attaatag                                            18

<210> SEQ ID NO 4
<211> LENGTH: 20
<212> TYPE: DNA
<213> ORGANISM: Artificial Sequence
<220> FEATURE:
<223> OTHER INFORMATION: synthetic construct; primer

<400> SEQUENCE: 4
ctacaaatgt ggtatggctg                                          20

<210> SEQ ID NO 5
<211> LENGTH: 31
<212> TYPE: DNA
<213> ORGANISM: Artificial Sequence
<220> FEATURE:
<223> OTHER INFORMATION: synthetic construct; primer

<400> SEQUENCE: 5
atcggatcca gggcgacacg gaaatgttga a                             31
```

<210> SEQ ID NO 6
<211> LENGTH: 32
<212> TYPE: DNA
<213> ORGANISM: Artificial Sequence
<220> FEATURE:
<223> OTHER INFORMATION: synthetic construct; primer

<400> SEQUENCE: 6
aatgcgcgct ggccgattca ttaatgcagc tg         32

<210> SEQ ID NO 7
<211> LENGTH: 31
<212> TYPE: DNA
<213> ORGANISM: Artificial Sequence
<220> FEATURE:
<223> OTHER INFORMATION: synthetic construct; primer

<400> SEQUENCE: 7
aatgcgcgca gggcgacacg gaaatgttga a          31

<210> SEQ ID NO 8
<211> LENGTH: 32
<212> TYPE: DNA
<213> ORGANISM: Artificial Sequence
<220> FEATURE:
<223> OTHER INFORMATION: synthetic construct; primer

<400> SEQUENCE: 8
atcactagtt ggccgattca ttaatgcagc tg         32

<210> SEQ ID NO 9
<211> LENGTH: 31
<212> TYPE: DNA
<213> ORGANISM: Artificial Sequence
<220> FEATURE:
<223> OTHER INFORMATION: synthetic construct; primer

<400> SEQUENCE: 9
atcactagta gggcgacacg gaaatgttga a          31

<210> SEQ ID NO 10
<211> LENGTH: 34
<212> TYPE: DNA
<213> ORGANISM: Artificial Sequence
<220> FEATURE:
<223> OTHER INFORMATION: synthetic construct; primer

<400> SEQUENCE: 10
atagcggccg ctggccgatt cattaatgca gctg       34

<210> SEQ ID NO 11
<211> LENGTH: 33
<212> TYPE: DNA
<213> ORGANISM: Artificial Sequence
<220> FEATURE:
<223> OTHER INFORMATION: synthetic construct; primer

<400> SEQUENCE: 11
atagcggccg cagggcgaca cggaaatgtt gaa        33

<210> SEQ ID NO 12
<211> LENGTH: 32
<212> TYPE: DNA
<213> ORGANISM: Artificial Sequence
<220> FEATURE:

<223> OTHER INFORMATION: synthetic construct; primer

<400> SEQUENCE: 12
cattctagat ggccgattca ttaatgcagc tg                        32

<210> SEQ ID NO 13
<211> LENGTH: 31
<212> TYPE: DNA
<213> ORGANISM: Artificial Sequence
<220> FEATURE:
<223> OTHER INFORMATION: synthetic construct; primer

<400> SEQUENCE: 13
cattctagaa gggcgacacg gaaatgttga a                         31

<210> SEQ ID NO 14
<211> LENGTH: 32
<212> TYPE: DNA
<213> ORGANISM: Artificial Sequence
<220> FEATURE:
<223> OTHER INFORMATION: synthetic construct; primer

<400> SEQUENCE: 14
aatctcgagt ggccgattca ttaatgcagc tg                        32

<210> SEQ ID NO 15
<211> LENGTH: 31
<212> TYPE: DNA
<213> ORGANISM: Artificial Sequence
<220> FEATURE:
<223> OTHER INFORMATION: synthetic construct; primer

<400> SEQUENCE: 15
aatctcgaga gggcgacacg gaaatgttga a                         31

<210> SEQ ID NO 16
<211> LENGTH: 32
<212> TYPE: DNA
<213> ORGANISM: Artificial Sequence
<220> FEATURE:
<223> OTHER INFORMATION: synthetic construct; primer

<400> SEQUENCE: 16
ataggtacct ggccgattca ttaatgcagc tg                        32

<210> SEQ ID NO 17
<211> LENGTH: 31
<212> TYPE: DNA
<213> ORGANISM: Artificial Sequence
<220> FEATURE:
<223> OTHER INFORMATION: synthetic construct; primer

<400> SEQUENCE: 17
cttactagta caagtttgta caaaaaagct g                         31

<210> SEQ ID NO 18
<211> LENGTH: 31
<212> TYPE: DNA
<213> ORGANISM: Artificial Sequence
<220> FEATURE:
<223> OTHER INFORMATION: synthetic construct; primer

<400> SEQUENCE: 18
catactagta ccactttgta caagaaagct g                         31

<210> SEQ ID NO 19
<211> LENGTH: 32
<212> TYPE: DNA
<213> ORGANISM: Artificial Sequence
<220> FEATURE:
<223> OTHER INFORMATION: synthetic construct; primer

<400> SEQUENCE: 19
tatcggtccg acaagtttgt acaaaaaagc tg                                    32

<210> SEQ ID NO 20
<211> LENGTH: 32
<212> TYPE: DNA
<213> ORGANISM: Artificial Sequence
<220> FEATURE:
<223> OTHER INFORMATION: synthetic construct; primer

<400> SEQUENCE: 20
tatcggtccg accactttgt acaagaaagc tg                                    32

<210> SEQ ID NO 21
<211> LENGTH: 24
<212> TYPE: DNA
<213> ORGANISM: Artificial Sequence
<220> FEATURE:
<223> OTHER INFORMATION: synthetic construct; primer

<400> SEQUENCE: 21
ttgtcgctgt acgcgggcaa acct                                             24

<210> SEQ ID NO 22
<211> LENGTH: 44
<212> TYPE: DNA
<213> ORGANISM: Artificial Sequence
<220> FEATURE:
<223> OTHER INFORMATION: synthetic construct; primer

<400> SEQUENCE: 22
aggtttgccc gcgtacagcg acaacatagt gactggatat gttg                       44

<210> SEQ ID NO 23
<211> LENGTH: 28
<212> TYPE: DNA
<213> ORGANISM: Artificial Sequence
<220> FEATURE:
<223> OTHER INFORMATION: synthetic construct; primer

<400> SEQUENCE: 23
atagctagcc cgggaccttt aattcaac                                         28

<210> SEQ ID NO 24
<211> LENGTH: 44
<212> TYPE: DNA
<213> ORGANISM: Artificial Sequence
<220> FEATURE:
<223> OTHER INFORMATION: synthetic construct; primer

<400> SEQUENCE: 24
agagtcgacc agtactccgg tctcctttga ttgtaaataa aatg                       44

<210> SEQ ID NO 25
<211> LENGTH: 40
<212> TYPE: DNA
<213> ORGANISM: Artificial Sequence
<220> FEATURE:
<223> OTHER INFORMATION: synthetic construct; primer

<400> SEQUENCE: 25
tattcgtctc agggaatatg caggtgaaaa acatattctc         40

<210> SEQ ID NO 26
<211> LENGTH: 39
<212> TYPE: DNA
<213> ORGANISM: Artificial Sequence
<220> FEATURE:
<223> OTHER INFORMATION: synthetic construct; primer

<400> SEQUENCE: 26
atatcgtctc gtattctagg caggtgggag aaaaaaatc          39

<210> SEQ ID NO 27
<211> LENGTH: 20
<212> TYPE: DNA
<213> ORGANISM: Artificial Sequence
<220> FEATURE:
<223> OTHER INFORMATION: synthetic construct; primer

<400> SEQUENCE: 27
cgtatttcga ctcgctcagg                              20

<210> SEQ ID NO 28
<211> LENGTH: 20
<212> TYPE: DNA
<213> ORGANISM: Artificial Sequence
<220> FEATURE:
<223> OTHER INFORMATION: synthetic construct; primer

<400> SEQUENCE: 28
cctgagcgag tcgaaatacg                              20

<210> SEQ ID NO 29
<211> LENGTH: 20
<212> TYPE: DNA
<213> ORGANISM: Artificial Sequence
<220> FEATURE:
<223> OTHER INFORMATION: synthetic construct; primer

<400> SEQUENCE: 29
gttttccgta gaatcgagac                              20

<210> SEQ ID NO 30
<211> LENGTH: 24
<212> TYPE: DNA
<213> ORGANISM: Artificial Sequence
<220> FEATURE:
<223> OTHER INFORMATION: synthetic construct; primer

<400> SEQUENCE: 30
gtaacatcag agattttgag acac                         24

<210> SEQ ID NO 31
<211> LENGTH: 12
<212> TYPE: DNA
<213> ORGANISM: Artificial Sequence
<220> FEATURE:
<223> OTHER INFORMATION: synthetic construct; primer

<400> SEQUENCE: 31
agcaaaagca gg                                      12

<210> SEQ ID NO 32
<211> LENGTH: 28

```
<212> TYPE: DNA
<213> ORGANISM: Artificial Sequence
<220> FEATURE:
<223> OTHER INFORMATION: synthetic construct; primer

<400> SEQUENCE: 32
tattggtctc agggagcaaa agcaggtc                                          28

<210> SEQ ID NO 33
<211> LENGTH: 35
<212> TYPE: DNA
<213> ORGANISM: Artificial Sequence
<220> FEATURE:
<223> OTHER INFORMATION: synthetic construct; primer

<400> SEQUENCE: 33
atatggtctc gtattagtag aaacaagggt cgttt                                  35

<210> SEQ ID NO 34
<211> LENGTH: 28
<212> TYPE: DNA
<213> ORGANISM: Artificial Sequence
<220> FEATURE:
<223> OTHER INFORMATION: synthetic construct; primer

<400> SEQUENCE: 34
tattcgtctc agggagcaaa agcaggca                                          28

<210> SEQ ID NO 35
<211> LENGTH: 34
<212> TYPE: DNA
<213> ORGANISM: Artificial Sequence
<220> FEATURE:
<223> OTHER INFORMATION: synthetic construct; primer

<400> SEQUENCE: 35
atatcgtctc gtattagtag aaacaagggc attt                                   34

<210> SEQ ID NO 36
<211> LENGTH: 29
<212> TYPE: DNA
<213> ORGANISM: Artificial Sequence
<220> FEATURE:
<223> OTHER INFORMATION: synthetic construct; primer

<400> SEQUENCE: 36
tattcgtctc agggagcaaa agcaggtac                                         29

<210> SEQ ID NO 37
<211> LENGTH: 34
<212> TYPE: DNA
<213> ORGANISM: Artificial Sequence
<220> FEATURE:
<223> OTHER INFORMATION: synthetic construct; primer

<400> SEQUENCE: 37
atatcgtctc gtattagtag aaacaagggt actt                                   34

<210> SEQ ID NO 38
<211> LENGTH: 28
<212> TYPE: DNA
<213> ORGANISM: Artificial Sequence
<220> FEATURE:
<223> OTHER INFORMATION: synthetic construct; primer

<400> SEQUENCE: 38
```

-continued tattcgtctc agggagcaaa agcagggg                                28

<210> SEQ ID NO 39
<211> LENGTH: 35
<212> TYPE: DNA
<213> ORGANISM: Artificial Sequence
<220> FEATURE:
<223> OTHER INFORMATION: synthetic construct; primer

<400> SEQUENCE: 39
atatcgtctc gtattagtag aaacaagggt gtttt                         35

<210> SEQ ID NO 40
<211> LENGTH: 29
<212> TYPE: DNA
<213> ORGANISM: Artificial Sequence
<220> FEATURE:
<223> OTHER INFORMATION: synthetic construct; primer

<400> SEQUENCE: 40
tattcgtctc agggagcaaa agcagggta                                29

<210> SEQ ID NO 41
<211> LENGTH: 37
<212> TYPE: DNA
<213> ORGANISM: Artificial Sequence
<220> FEATURE:
<223> OTHER INFORMATION: synthetic construct; primer

<400> SEQUENCE: 41
atatcgtctc gtattagtag aaacaagggt atttttt                       37

<210> SEQ ID NO 42
<211> LENGTH: 29
<212> TYPE: DNA
<213> ORGANISM: Artificial Sequence
<220> FEATURE:
<223> OTHER INFORMATION: synthetic construct; primer

<400> SEQUENCE: 42
tattggtctc agggagcaaa agcaggagt                                29

<210> SEQ ID NO 43
<211> LENGTH: 37
<212> TYPE: DNA
<213> ORGANISM: Artificial Sequence
<220> FEATURE:
<223> OTHER INFORMATION: synthetic construct; primer

<400> SEQUENCE: 43
atatggtctc gtattagtag aaacaaggga gtttttt                       37

<210> SEQ ID NO 44
<211> LENGTH: 29
<212> TYPE: DNA
<213> ORGANISM: Artificial Sequence
<220> FEATURE:
<223> OTHER INFORMATION: synthetic construct; primer

<400> SEQUENCE: 44
tattcgtctc agggagcaaa agcaggtag                                29

<210> SEQ ID NO 45
<211> LENGTH: 37
<212> TYPE: DNA
<213> ORGANISM: Artificial Sequence

```
<220> FEATURE:
<223> OTHER INFORMATION: synthetic construct; primer

<400> SEQUENCE: 45
atatcgtctc gtattagtag aaacaagggt agttttt                              37

<210> SEQ ID NO 46
<211> LENGTH: 29
<212> TYPE: DNA
<213> ORGANISM: Artificial Sequence
<220> FEATURE:
<223> OTHER INFORMATION: synthetic construct; primer

<400> SEQUENCE: 46
tattcgtctc agggagcaaa agcagggtg                                       29

<210> SEQ ID NO 47
<211> LENGTH: 20
<212> TYPE: DNA
<213> ORGANISM: Artificial Sequence
<220> FEATURE:
<223> OTHER INFORMATION: synthetic construct; primer

<400> SEQUENCE: 47
tcaatgatgt gggagattaa                                                 20

<210> SEQ ID NO 48
<211> LENGTH: 20
<212> TYPE: DNA
<213> ORGANISM: Artificial Sequence
<220> FEATURE:
<223> OTHER INFORMATION: synthetic construct; primer

<400> SEQUENCE: 48
ggaatgatga tgggcatgtt                                                 20

<210> SEQ ID NO 49
<211> LENGTH: 23
<212> TYPE: DNA
<213> ORGANISM: Artificial Sequence
<220> FEATURE:
<223> OTHER INFORMATION: synthetic construct; primer

<400> SEQUENCE: 49
ttaagcattg aggacccaag tca                                             23

<210> SEQ ID NO 50
<211> LENGTH: 21
<212> TYPE: DNA
<213> ORGANISM: Artificial Sequence
<220> FEATURE:
<223> OTHER INFORMATION: synthetic construct; primer

<400> SEQUENCE: 50
tgaactatta ctggaccttg c                                               21

<210> SEQ ID NO 51
<211> LENGTH: 20
<212> TYPE: DNA
<213> ORGANISM: Artificial Sequence
<220> FEATURE:
<223> OTHER INFORMATION: synthetic construct; primer

<400> SEQUENCE: 51
gctttccact agaggagttc                                                 20
```

<210> SEQ ID NO 52
<211> LENGTH: 24
<212> TYPE: DNA
<213> ORGANISM: Artificial Sequence
<220> FEATURE:
<223> OTHER INFORMATION: synthetic construct; primer

<400> SEQUENCE: 52
caagatcgaa aagggggaagg ttac                                             24

<210> SEQ ID NO 53
<211> LENGTH: 21
<212> TYPE: DNA
<213> ORGANISM: Artificial Sequence
<220> FEATURE:
<223> OTHER INFORMATION: synthetic construct; primer

<400> SEQUENCE: 53
cctatcagaa acgaatgggg g                                                 21

<210> SEQ ID NO 54
<211> LENGTH: 21
<212> TYPE: DNA
<213> ORGANISM: Artificial Sequence
<220> FEATURE:
<223> OTHER INFORMATION: synthetic construct; primer

<400> SEQUENCE: 54
gggctttcac cgaagaggga g                                                 21

<210> SEQ ID NO 55
<211> LENGTH: 42
<212> TYPE: DNA
<213> ORGANISM: Artificial Sequence
<220> FEATURE:
<223> OTHER INFORMATION: synthetic construct; primer

<400> SEQUENCE: 55
acagccctca aactgaaact agaggactat ttggagctat ag                          42

<210> SEQ ID NO 56
<211> LENGTH: 21
<212> TYPE: DNA
<213> ORGANISM: Artificial Sequence
<220> FEATURE:
<223> OTHER INFORMATION: synthetic construct; primer

<400> SEQUENCE: 56
aggatatagc gggagttttg t                                                 21

<210> SEQ ID NO 57
<211> LENGTH: 24
<212> TYPE: DNA
<213> ORGANISM: Artificial Sequence
<220> FEATURE:
<223> OTHER INFORMATION: synthetic construct; primer

<400> SEQUENCE: 57
attggatcca ccatggtgag caag                                              24

<210> SEQ ID NO 58
<211> LENGTH: 26
<212> TYPE: DNA
<213> ORGANISM: Artificial Sequence
<220> FEATURE:
<223> OTHER INFORMATION: synthetic construct; primer

```
<400> SEQUENCE: 58
atcgaattct tacttgtaca gctcgt                                          26

<210> SEQ ID NO 59
<211> LENGTH: 8
<212> TYPE: PRT
<213> ORGANISM: Artificial Sequence
<220> FEATURE:
<223> OTHER INFORMATION: synthetic construct; cleavage site

<400> SEQUENCE: 59

Arg Glu Arg Arg Arg Lys Lys Arg
1               5

<210> SEQ ID NO 60
<211> LENGTH: 150
<212> TYPE: DNA
<213> ORGANISM: Artificial Sequence
<220> FEATURE:
<223> OTHER INFORMATION: synthetic construct; pFastBac1

<400> SEQUENCE: 60
tagatcatgg agataattaa aatgataacc atctcgcaaa taaataagta ttttactgtt     60
ttcgtaacag ttttgtaata aaaaaaccta taaatattcc ggattattca taccgtccca    120
ccatcgggcg cggatcccgg tccgaagcgc                                     150

<210> SEQ ID NO 61
<211> LENGTH: 22
<212> TYPE: DNA
<213> ORGANISM: Artificial Sequence
<220> FEATURE:
<223> OTHER INFORMATION: synthetic construct; pFast-Delp1h

<400> SEQUENCE: 61
tagggatccc ggtccgaagc gc                                              22

<210> SEQ ID NO 62
<211> LENGTH: 22
<212> TYPE: DNA
<213> ORGANISM: Artificial Sequence
<220> FEATURE:
<223> OTHER INFORMATION: synthetic construct; No. 6 pFAST-Dp1h.seq

<400> SEQUENCE: 62
tagggatccc ggtccgaagc gc                                              22

<210> SEQ ID NO 63
<211> LENGTH: 129
<212> TYPE: DNA
<213> ORGANISM: Artificial Sequence
<220> FEATURE:
<223> OTHER INFORMATION: synthetic construct; p1h promoter.seq

<400> SEQUENCE: 63
atcatggaga taattaaaat gataaccatc tcgcaaataa ataagtattt tactgttttc     60
gtaacagttt tgtaataaaa aaacctataa atattccgga ttattcatac cgtcccacca    120
tcgggcgcg                                                            129
```